United States Patent
Loerz et al.

(10) Patent No.: US 6,951,969 B1
(45) Date of Patent: Oct. 4, 2005

(54) NUCLEIC ACID MOLECULES WHICH CODE FOR ENZYMES DERIVED FROM WHEAT AND WHICH ARE INVOLVED IN THE SYNTHESIS OF STARCH

(75) Inventors: Horst Loerz, Hamburg (DE); Stephanie Luetticke, Hamburg (DE); Gernot Abel, Copenhagen (DK); Ulrich Genschel, Hamburg (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 09/674,817

(22) PCT Filed: May 7, 1999

(86) PCT No.: PCT/EP99/03141

§ 371 (c)(1),
(2), (4) Date: Nov. 6, 2000

(87) PCT Pub. No.: WO99/58690

PCT Pub. Date: Nov. 18, 1999

(30) Foreign Application Priority Data

May 8, 1998 (DE) .......................... 198 20 608

(51) Int. Cl.[7] .................. C12N 15/82; C12N 15/29; C12N 15/87; C12N 15/56; A01H 5/00
(52) U.S. Cl. .............. 800/278; 800/287; 800/298; 800/320; 800/320.1; 800/284; 536/23.6; 536/23.1; 536/24.1; 435/320.1; 435/69.1; 435/468; 435/419; 435/201
(58) Field of Search ................ 536/23.6, 23.1, 536/24.1; 800/287, 278, 284, 298, 320.1, 320; 435/320.1, 201, 69.1, 468, 419, 101

(56) References Cited

U.S. PATENT DOCUMENTS 5,405,765 A * 4/1995 Vasil et al. .............. 435/172.3
RE35,202 E * 4/1996 Baltensperger et al. ........ 241/9
6,130,367 A * 10/2000 Kossmann et al. ......... 800/284

FOREIGN PATENT DOCUMENTS

WO  WO 96/03513  2/1996
WO  WO 99/14314  3/1999

OTHER PUBLICATIONS

Bowie et al (1990, Science 247:1306–10).*
McConnell et al (2001, Nature 411 (6838):709–713).*
Fourgoux–Nicol et al (1999, Plant Molecular Biology 40 : 857–872).*
Kossmann et al (1995, Carbohydrate Bioengineering, S.B. Petersen, B. Svensson and S Pedersen (Eds). pp. 271–278).*
Willmitzer et al (1993 In Plant Polymeric Carbohydrates; International Symposium Meuser, F., D.J. Manners and W. Seibel (Eds) Starch synthesis in transgenic plants, pp. 33–39).*
Plant Gene Register PGR 97–187, Genomic Nucleotide Sequence of a Full–length Wild–type Allele of the Maize Sugaryl (Sul) Gene (Accession No. AF030882).
James et al., "Characterization of the Maize Gene sugaryl, a Determinant of Starch Composition in Kernels", The Plant Cell, vol. 7, 417–429, Apr. 1995.
James et al., "Zea mays sulp (Sugaryl) mRNA, partial cds", EMBL Nucelotide Sequence, U18908, Apr. 19, 1995, (XP002084161).

* cited by examiner

Primary Examiner—David T. Fox
Assistant Examiner—Stuart F. Baum
(74) Attorney, Agent, or Firm—Frommer Lawrence & Haug LLP

(57) ABSTRACT

Nucleic acid molecules are described which encode enzymes involved in starch synthasis in plants. These enzymes are wheat isoamylases.

The invention furthermore relates to vectors and host cells which contain the above-described nucleic acid molecules, in particular to transformed plant cells and plants which can be regenerated from these and which have an increased or reduced activity of the isoamylases according to the invention.

20 Claims, No Drawings

SEQUENCE LISTING

<160> NUMBER OF SEQ ID NOS: 11

<210> SEQ ID NO 1
<211> LENGTH: 2997
<212> TYPE: DNA
<213> ORGANISM: Triticum aestivum L. cv.Florida
<220> FEATURE:
<221> NAME/KEY: CDS
<222> LOCATION: (3)..(296)
<223> OTHER INFORMATION:
<220> FEATURE:
<221> NAME/KEY: CDS
<222> LOCATION: (397)..(1617)
<223> OTHER INFORMATION:
<220> FEATURE:
<221> NAME/KEY: CDS
<222> LOCATION: (2145)..(2960)
<223> OTHER INFORMATION:

<400> SEQUENCE: 1

```
gg tcg ggg ccg gcg ccg cgc ctg cga cgg tgg cga ccc aat gcg acg        47
   Ser Gly Pro Ala Pro Arg Leu Arg Arg Trp Arg Pro Asn Ala Thr
   1               5                   10                  15 gcg ggg aag ggg gtc ggc gag gtg tgc gcc gcg gtt gtc gag gcg gcg        95
Ala Gly Lys Gly Val Gly Glu Val Cys Ala Ala Val Val Glu Ala Ala
                20                  25                  30 acg aag gta gag gac gag ggg gag gag gac gag ccg gtg gcg gag gac       143
Thr Lys Val Glu Asp Glu Gly Glu Glu Asp Glu Pro Val Ala Glu Asp
            35                  40                  45 agg tac gcg ctc ggc ggc gcg tgc agg gtg ctc gcc gga atg ccc gcg       191
Arg Tyr Ala Leu Gly Gly Ala Cys Arg Val Leu Ala Gly Met Pro Ala
        50                  55                  60 ccg ctg ggc gcc acc gcg ctc gcc ggc ggg gtc aat ttc gcc gtc tat       239
Pro Leu Gly Ala Thr Ala Leu Ala Gly Gly Val Asn Phe Ala Val Tyr
    65                  70                  75 tcc ggc gga gcc acc gcc gcg gcg ctc tgc ctc ttc acg cca gaa gat       287
Ser Gly Gly Ala Thr Ala Ala Ala Leu Cys Leu Phe Thr Pro Glu Asp
80                  85                  90                  95 ctc aag gcg gtggggttgc tcccgagta gagttcatca gctttgcgtg               336
Leu Lys Ala cgccgcgcgc ccctttttg ggcctgcaat ttaagttttg tactggggca aatgctgcag     396 gat agg gtg acc gag gag gtt ccc ctt gac ccc ctg atg aat cgg acc       444
Asp Arg Val Thr Glu Glu Val Pro Leu Asp Pro Leu Met Asn Arg Thr
        100                 105                 110 ggg aac gtg tgg cat gtc ttc atc gaa ggc gag ctg cac aac atg ctt       492
Gly Asn Val Trp His Val Phe Ile Glu Gly Glu Leu His Asn Met Leu
115                 120                 125                 130 tac ggg tac agg ttc gac ggc acc ttt gct cct cac tgc ggg cac tac       540
Tyr Gly Tyr Arg Phe Asp Gly Thr Phe Ala Pro His Cys Gly His Tyr
            135                 140                 145 ctt gat gtt tcc aat gtc gtg gtg gat cct tat gct aag gca gtg ata       588
Leu Asp Val Ser Asn Val Val Val Asp Pro Tyr Ala Lys Ala Val Ile
        150                 155                 160 agc cga ggg gag tat ggt gtt cca gcg cgt ggt aac aat tgc tgg cct       636
Ser Arg Gly Glu Tyr Gly Val Pro Ala Arg Gly Asn Asn Cys Trp Pro
    165                 170                 175 cag atg gct ggc atg atc cct ctt cca tat agc acg ttt gat tgg gaa       684
Gln Met Ala Gly Met Ile Pro Leu Pro Tyr Ser Thr Phe Asp Trp Glu
180                 185                 190
```

```
ggc gac cta cct cta aga tat cct caa aag gac ctg gta ata tat gag    732
Gly Asp Leu Pro Leu Arg Tyr Pro Gln Lys Asp Leu Val Ile Tyr Glu
195                 200                 205                 210 atg cac ttg cgt gga ttc acg aag cat gat tca agc aat gta gaa cat    780
Met His Leu Arg Gly Phe Thr Lys His Asp Ser Ser Asn Val Glu His
            215                 220                 225 ccg ggt act ttc att gga gct gtg tcg aag ctt gac tat ttg aag gag    828
Pro Gly Thr Phe Ile Gly Ala Val Ser Lys Leu Asp Tyr Leu Lys Glu
            230                 235                 240 ctt gga gtt aat tgt att gaa tta atg ccc tgc cat gag ttc aac gag    876
Leu Gly Val Asn Cys Ile Glu Leu Met Pro Cys His Glu Phe Asn Glu
            245                 250                 255 ctg gag tac tca acc tct tct tcc aag atg aac ttt tgg gga tat tct    924
Leu Glu Tyr Ser Thr Ser Ser Ser Lys Met Asn Phe Trp Gly Tyr Ser
260                 265                 270 acc ata aac ttc ttt tca cca atg aca aga tac aca tca ggc ggg ata    972
Thr Ile Asn Phe Phe Ser Pro Met Thr Arg Tyr Thr Ser Gly Gly Ile
275                 280                 285                 290 aaa aac tgt ggg cgt gat gcc ata aat gag ttc aaa act ttt gta aga   1020
Lys Asn Cys Gly Arg Asp Ala Ile Asn Glu Phe Lys Thr Phe Val Arg
                295                 300                 305 gag gct cac aaa cgg gga att gag gtg atc ctg gat gtt gtc ttc aac   1068
Glu Ala His Lys Arg Gly Ile Glu Val Ile Leu Asp Val Val Phe Asn
            310                 315                 320 cat aca gct gag ggt aat gag aat ggt cca ata tta tca ttt aag ggg   1116
His Thr Ala Glu Gly Asn Glu Asn Gly Pro Ile Leu Ser Phe Lys Gly
            325                 330                 335 gtc gat aat act aca tac tat atg ctt gca ccc aag gga gag ttt tat   1164
Val Asp Asn Thr Thr Tyr Tyr Met Leu Ala Pro Lys Gly Glu Phe Tyr
340                 345                 350 aac tat tct ggc tgt ggg aat acc ttc aac tgt aat cat cct gtg gtt   1212
Asn Tyr Ser Gly Cys Gly Asn Thr Phe Asn Cys Asn His Pro Val Val
355                 360                 365                 370 cgt caa ttc att gta gat tgt tta aga tac tgg gtg acg gaa atg cat   1260
Arg Gln Phe Ile Val Asp Cys Leu Arg Tyr Trp Val Thr Glu Met His
                375                 380                 385 gtt gat ggt ttt cgt ttt gat ctt gca tcc ata atg acc aga ggt tcc   1308
Val Asp Gly Phe Arg Phe Asp Leu Ala Ser Ile Met Thr Arg Gly Ser
            390                 395                 400 agt ctg tgg gat cca gtt aac gtg tat gga gct cca ata gaa ggt gac   1356
Ser Leu Trp Asp Pro Val Asn Val Tyr Gly Ala Pro Ile Glu Gly Asp
            405                 410                 415 atg atc aca aca ggg aca cct ctt gtt act cca cca ctt att gac atg   1404
Met Ile Thr Thr Gly Thr Pro Leu Val Thr Pro Pro Leu Ile Asp Met
420                 425                 430 atc agc aat gac cca att ctt gga ggc gtc aag ctc att gct gaa gca   1452
Ile Ser Asn Asp Pro Ile Leu Gly Gly Val Lys Leu Ile Ala Glu Ala
435                 440                 445                 450 tgg gat gca gga ggc ctc tat caa gta ggt caa ttc cct cac tgg aat   1500
Trp Asp Ala Gly Gly Leu Tyr Gln Val Gly Gln Phe Pro His Trp Asn
                455                 460                 465 gtt tgg tct gag tgg aat ggg aag tac cgg gac att gtg cgt caa ttc   1548
Val Trp Ser Glu Trp Asn Gly Lys Tyr Arg Asp Ile Val Arg Gln Phe
            470                 475                 480 att aaa ggc act gat gga ttt gct ggt ggt ttt gcc gaa tgt ctt tgt   1596
Ile Lys Gly Thr Asp Gly Phe Ala Gly Gly Phe Ala Glu Cys Leu Cys
            485                 490                 495 gga agt cca cac cta tac cag gtaagttgtg gcaatacttg taaatgagtt      1647
Gly Ser Pro His Leu Tyr Gln
500                 505
```

-continued

```
gagtgaatgt cacctggatt ttttatatat accacatgat gatacacatc taaatatata    1707
acaatcatag tgtatgcata tgcatttggc taagaagtat tagtgtatac actagtgcta    1767
tatataggtt ttaacaccca acttgccaat gaaggaacat agggctttct agttatctta    1827
tttatttgtc cggtgaataa tccactgaaa aattccagcc atgtcatttt ttaggggggg    1887
agaagaaact atattgattt gcccccctaa aagaagccat ctcagaattc ataggtaagt    1947
tgcttttctg taaagaaagg aaaacgactt catactttct atcggtgcta acttagctcg    2007
atgtatattt gtaagatgaa tgccaaattt aatttgtcgg ataatttgat ctgttattca    2067
caaatttcta tttggtttct ctagaaatca aaccagtaac ttgttattgg cactgcaact    2127
tcttattgat taatcag gca gga gga agg aaa cct tgg cac agt atc aac      2177
                    Ala Gly Gly Arg Lys Pro Trp His Ser Ile Asn
                                510                 515 ttt gta tgt gca cat gat gga ttt aca ctg gct gat ttg gta aca tat     2225
Phe Val Cys Ala His Asp Gly Phe Thr Leu Ala Asp Leu Val Thr Tyr
            520                 525                 530 aat aag aag tac aat tta cca aat ggg gag aac aac aga gat gga gaa     2273
Asn Lys Lys Tyr Asn Leu Pro Asn Gly Glu Asn Asn Arg Asp Gly Glu
        535                 540                 545 aat cac aat ctt agc tgg aat tgt ggg gag gaa gga gaa ttc gca aga     2321
Asn His Asn Leu Ser Trp Asn Cys Gly Glu Glu Gly Glu Phe Ala Arg
    550                 555                 560 ttg tct gtc aaa aga ttg agg aag agg cag atg cgc aat ttc ttt gtt     2369
Leu Ser Val Lys Arg Leu Arg Lys Arg Gln Met Arg Asn Phe Phe Val
565                 570                 575                 580 tgt ctc atg gtt tct caa gga gtt cca atg ttc tac atg ggt gat gaa     2417
Cys Leu Met Val Ser Gln Gly Val Pro Met Phe Tyr Met Gly Asp Glu
            585                 590                 595 tat ggc cac aca aaa ggg ggc aac aac aat aca tac tgc cat gat tct     2465
Tyr Gly His Thr Lys Gly Gly Asn Asn Asn Thr Tyr Cys His Asp Ser
        600                 605                 610 tat gtc aat tat ttt cgc tgg gat aaa aaa gaa caa tac tct gag ttg     2513
Tyr Val Asn Tyr Phe Arg Trp Asp Lys Lys Glu Gln Tyr Ser Glu Leu
    615                 620                 625 cac cga ttc tgc tgc ctc atg acc aaa ttc cgc aag gag tgc gag ggt     2561
His Arg Phe Cys Cys Leu Met Thr Lys Phe Arg Lys Glu Cys Glu Gly
630                 635                 640 ctt ggc ctt gag gac ttt cca acg gcc aaa cgg ctg cag tgg cat ggt     2609
Leu Gly Leu Glu Asp Phe Pro Thr Ala Lys Arg Leu Gln Trp His Gly
645                 650                 655                 660 cat cag cct ggg aag cct gat tgg tct gag aat agc cga ttc gtt gcc     2657
His Gln Pro Gly Lys Pro Asp Trp Ser Glu Asn Ser Arg Phe Val Ala
            665                 670                 675 ttt tcc atg aaa gat gaa aga cag ggc gag atc tat gtg gcc ttc aac     2705
Phe Ser Met Lys Asp Glu Arg Gln Gly Glu Ile Tyr Val Ala Phe Asn
        680                 685                 690 acc agc cac tta ccg gcc gtt gtt gag ctc cca gag cgc gca ggg cgc     2753
Thr Ser His Leu Pro Ala Val Val Glu Leu Pro Glu Arg Ala Gly Arg
    695                 700                 705 cgg tgg gaa ccg gtg gtg gac aca ggc aag cca gca cca tac gac ttc     2801
Arg Trp Glu Pro Val Val Asp Thr Gly Lys Pro Ala Pro Tyr Asp Phe
710                 715                 720 ctc acc gac gac tta cct gat cgc gct ctc acc ata cac cag ttc tcg     2849
Leu Thr Asp Asp Leu Pro Asp Arg Ala Leu Thr Ile His Gln Phe Ser
725                 730                 735                 740 cat ttc ctc tac tcc aac ctc tac ccc atg ctc agc tac tca tcg gtc     2897
His Phe Leu Tyr Ser Asn Leu Tyr Pro Met Leu Ser Tyr Ser Ser Val
            745                 750                 755
```

| | | | | | | | | | | | | |
|---|---|---|---|---|---|---|---|---|---|---|---|---|
| atc | cta | gta | ttg | cgc | cct | gat | gtt | tga | gag | acc | aat | ata | tac | agt | aaa | 2945 |
| Ile | Leu | Val | Leu | Arg | Pro | Asp | Val | | Glu | Thr | Asn | Ile | Tyr | Ser | Lys | |
| | | | 760 | | | | | | | 765 | | | | 770 | | | taa tat gtc tat atg taaaaaaaaa aaaaaaaaaa aaaaaaaaaa aaaaaaa    2997
    Tyr Val Tyr Met
                775

<210> SEQ ID NO 2
<211> LENGTH: 2997
<212> TYPE: DNA
<213> ORGANISM: Triticum asetivum L. cvFlorida

<400> SEQUENCE: 2

| | |
|---|---|
| ggtcggggcc ggcgccgcgc ctgcgacggt ggcgacccaa tgcgacggcg gggaaggggg | 60 |
| tcggcgaggt gtgcgccgcg gttgtcgagg cggcgacgaa ggtagaggac gaggggggagg | 120 |
| aggacgagcc ggtggcggag gacaggtacg cgctcggcgg cgcgtgcagg gtgctcgccg | 180 |
| gaatgcccgc gccgctgggc gccaccgcgc tcgccggcgg ggtcaatttc gccgtctatt | 240 |
| ccggcggagc caccgccgcg gcgctctgcc tcttcacgcc agaagatctc aaggcggtgg | 300 |
| ggttgcctcc cgagtagagt tcatcagctt gcgtgcgcc gcgcgcccct tttttgggcc | 360 |
| tgcaatttaa gttttgtact ggggcaaatg ctgcaggata gggtgaccga ggaggttccc | 420 |
| cttgacccc tgatgaatcg gacccgggaac gtgtggcatg tcttcatcga aggcgagctg | 480 |
| cacaacatgc tttacgggta caggttcgac ggcacctttg ctcctcactg cgggcactac | 540 |
| cttgatgttt ccaatgtcgt ggtggatcct tatgctaagg cagtgataag ccgagggggag | 600 |
| tatggtgttc cagcgcgtgg taacaattgc tggcctcaga tggctggcat gatccctctt | 660 |
| ccatatagca cgtttgattg ggaaggcgac ctacctctaa gatatcctca aaaggacctg | 720 |
| gtaatatatg agatgcactt gcgtggattc acgaagcatg attcaagcaa tgtagaacat | 780 |
| ccgggtactt tcattggagc tgtgtcgaag cttgactatt tgaaggagct tggagttaat | 840 |
| tgtattgaat taatgccctg ccatgagttc aacgagctgg agtactcaac ctcttcttcc | 900 |
| aagatgaact tttgggggata ttctaccata aacttctttt caccaatgac aagatacaca | 960 |
| tcaggcggga taaaaaactg tgggcgtgat gccataaatg agttcaaaac ttttgtaaga | 1020 |
| gaggctcaca acggggaat tgaggtgatc ctggatgttg tcttcaacca tacagctgag | 1080 |
| ggtaatgaga atggtccaat attatcattt aaggggggtcg ataatactac atactatatg | 1140 |
| cttgcaccca agggagagtt ttataactat tctggctgtg ggaataccttt caactgtaat | 1200 |
| catcctgtgg ttcgtcaatt cattgtagat tgtttaagat actgggtgac ggaaatgcat | 1260 |
| gttgatggtt ttcgttttga tcttgcatcc ataatgacca gaggttccag tctgtgggat | 1320 |
| ccagttaacg tgtatggagc tccaatagaa ggtgacatga tcacaacagg gacacctctt | 1380 |
| gttactccac cacttattga catgatcagc aatgacccaa ttcttggagg cgtcaagctc | 1440 |
| attgctgaag catgggatgc aggaggcctc tatcaagtag gtcaattccc tcactggaat | 1500 |
| gtttggtctg agtggaatgg gaagtaccgg gacattgtgc gtcaattcat taaaggcact | 1560 |
| gatggatttg ctggtggttt tgccgaatgt ctttgtggaa gtccacacct ataccaggta | 1620 |
| agttgtggca atacttgtaa atgagttgag tgaatgtcac ctggattttt tatatatacc | 1680 |
| acatgatgat acacatctaa atatataaca atcatagtgt atgcatatgc atttggctaa | 1740 |
| gaagtattag tgtatacact agtgctatat ataggtttta acacccaact tgccaatgaa | 1800 |
| ggaacatagg gctttctagt tatcttattt atttgtccgg tgaataatcc actgaaaat | 1860 |
| tccagccatg tcattttttta gggggggagaa agaaactata ttgatttgcc ccctaaaag | 1920 |

-continued

```
aagccatctc agaattcata ggtaagttgc tttctgtaa agaaaggaaa acgacttcat    1980
actttctatc ggtgctaact tagctcgatg tatatttgta agatgaatgc caaatttaat    2040
ttgtcggata atttgatctg ttattcacaa atttctattt ggtttctcta gaaatcaaac    2100
cagtaacttg ttattggcac tgcaacttct tattgattaa tcaggcagga ggaaggaaac    2160
cttggcacag tatcaacttt gtatgtgcac atgatggatt tacactggct gatttggtaa    2220
catataataa gaagtacaat ttaccaaatg gggagaacaa cagagatgga gaaaatcaca    2280
atcttagctg gaattgtggg gaggaaggag aattcgcaag attgtctgtc aaagattga    2340 ggaagaggca gatgcgcaat ttctttgttt gtctcatggt ttctcaagga gttccaatgt    2400
tctacatggg tgatgaatat ggccacacaa aaggggcaa caacaataca tactgccatg    2460
attcttatgt caattatttt cgctgggata aaaagaaca atactctgag ttgcaccgat    2520
tctgctgcct catgaccaaa ttccgcaagg agtgcgaggg tcttggcctt gaggactttc    2580
caacggccaa acggctgcag tggcatggtc atcagcctgg gaagcctgat tggtctgaga    2640
atagccgatt cgttgccttt tccatgaaag atgaaagaca gggcgagatc tatgtggcct    2700
tcaacaccag ccacttaccg gccgttgttg agctcccaga gcgcgcaggg cgccggtggg    2760
aaccggtggt ggacacaggc aagccagcac catacgactt cctcaccgac gacttacctg    2820
atcgcgctct caccatacac cagttctcgc atttcctcta ctccaacctc taccccatgc    2880
tcagctactc atcggtcatc ctagtattgc gccctgatgt ttgagagacc aatatataca    2940
gtaaataata tgtctatatg taaaaaaaa aaaaaaaaa aaaaaaaaa aaaaaaa         2997
```

<210> SEQ ID NO 3
<211> LENGTH: 764
<212> TYPE: PRT
<213> ORGANISM: Triticum aestivum L. cv.Florida

<400> SEQUENCE: 3

```
Ser Gly Pro Ala Pro Arg Leu Arg Arg Trp Arg Pro Asn Ala Thr Ala
1               5                   10                  15

Gly Lys Gly Val Gly Glu Val Cys Ala Ala Val Val Glu Ala Ala Thr
            20                  25                  30

Lys Val Glu Asp Glu Gly Glu Glu Asp Glu Pro Val Ala Glu Asp Arg
        35                  40                  45

Tyr Ala Leu Gly Gly Ala Cys Arg Val Leu Ala Gly Met Pro Ala Pro
    50                  55                  60

Leu Gly Ala Thr Ala Leu Ala Gly Gly Val Asn Phe Ala Val Tyr Ser
65                  70                  75                  80

Gly Gly Ala Thr Ala Ala Ala Leu Cys Leu Phe Thr Pro Glu Asp Leu
                85                  90                  95

Lys Ala Asp Arg Val Thr Glu Glu Val Pro Leu Asp Pro Leu Met Asn
            100                 105                 110

Arg Thr Gly Asn Val Trp His Val Phe Ile Glu Gly Glu Leu His Asn
        115                 120                 125

Met Leu Tyr Gly Tyr Arg Phe Asp Gly Thr Phe Ala Pro His Cys Gly
    130                 135                 140

His Tyr Leu Asp Val Ser Asn Val Val Asp Pro Tyr Ala Lys Ala
145                 150                 155                 160

Val Ile Ser Arg Gly Glu Tyr Gly Val Pro Ala Arg Gly Asn Asn Cys
                165                 170                 175

Trp Pro Gln Met Ala Gly Met Ile Pro Leu Pro Tyr Ser Thr Phe Asp
            180                 185                 190
```

-continued

```
Trp Glu Gly Asp Leu Pro Leu Arg Tyr Pro Gln Lys Asp Leu Val Ile
    195                 200                 205

Tyr Glu Met His Leu Arg Gly Phe Thr Lys His Asp Ser Ser Asn Val
    210                 215                 220

Glu His Pro Gly Thr Phe Ile Gly Ala Val Ser Lys Leu Asp Tyr Leu
225                 230                 235                 240

Lys Glu Leu Gly Val Asn Cys Ile Glu Leu Met Pro Cys His Glu Phe
                245                 250                 255

Asn Glu Leu Glu Tyr Ser Thr Ser Ser Lys Met Asn Phe Trp Gly
                260                 265                 270

Tyr Ser Thr Ile Asn Phe Phe Ser Pro Met Thr Arg Tyr Thr Ser Gly
    275                 280                 285

Gly Ile Lys Asn Cys Gly Arg Asp Ala Ile Asn Glu Phe Lys Thr Phe
    290                 295                 300

Val Arg Glu Ala His Lys Arg Gly Ile Glu Val Ile Leu Asp Val Val
305                 310                 315                 320

Phe Asn His Thr Ala Glu Gly Asn Glu Asn Gly Pro Ile Leu Ser Phe
                325                 330                 335

Lys Gly Val Asp Asn Thr Thr Tyr Tyr Met Leu Ala Pro Lys Gly Glu
                340                 345                 350

Phe Tyr Asn Tyr Ser Gly Cys Gly Asn Thr Phe Asn Cys Asn His Pro
                355                 360                 365

Val Val Arg Gln Phe Ile Val Asp Cys Leu Arg Tyr Trp Val Thr Glu
    370                 375                 380

Met His Val Asp Gly Phe Arg Phe Asp Leu Ala Ser Ile Met Thr Arg
385                 390                 395                 400

Gly Ser Ser Leu Trp Asp Pro Val Asn Val Tyr Gly Ala Pro Ile Glu
                405                 410                 415

Gly Asp Met Ile Thr Thr Gly Thr Pro Leu Val Thr Pro Pro Leu Ile
                420                 425                 430

Asp Met Ile Ser Asn Asp Pro Ile Leu Gly Gly Val Lys Leu Ile Ala
            435                 440                 445

Glu Ala Trp Asp Ala Gly Gly Leu Tyr Gln Val Gly Gln Phe Pro His
    450                 455                 460

Trp Asn Val Trp Ser Glu Trp Asn Gly Lys Tyr Arg Asp Ile Val Arg
465                 470                 475                 480

Gln Phe Ile Lys Gly Thr Asp Gly Phe Ala Gly Gly Phe Ala Glu Cys
                485                 490                 495

Leu Cys Gly Ser Pro His Leu Tyr Gln Ala Gly Gly Arg Lys Pro Trp
                500                 505                 510

His Ser Ile Asn Phe Val Cys Ala His Asp Gly Phe Thr Leu Ala Asp
    515                 520                 525

Leu Val Thr Tyr Asn Lys Lys Tyr Asn Leu Pro Asn Gly Glu Asn Asn
    530                 535                 540

Arg Asp Gly Glu Asn His Asn Leu Ser Trp Asn Cys Gly Glu Glu Gly
545                 550                 555                 560

Glu Phe Ala Arg Leu Ser Val Lys Arg Leu Arg Lys Arg Gln Met Arg
                565                 570                 575

Asn Phe Phe Val Cys Leu Met Val Ser Gln Gly Val Pro Met Phe Tyr
                580                 585                 590

Met Gly Asp Glu Tyr Gly His Thr Lys Gly Gly Asn Asn Asn Thr Tyr
                595                 600                 605
```

-continued

```
Cys His Asp Ser Tyr Val Asn Tyr Phe Arg Trp Asp Lys Lys Glu Gln
    610                 615                 620
Tyr Ser Glu Leu His Arg Phe Cys Cys Leu Met Thr Lys Phe Arg Lys
625                 630                 635                 640
Glu Cys Glu Gly Leu Gly Leu Glu Asp Phe Pro Thr Ala Lys Arg Leu
                645                 650                 655
Gln Trp His Gly His Gln Pro Gly Lys Pro Asp Trp Ser Glu Asn Ser
            660                 665                 670
Arg Phe Val Ala Phe Ser Met Lys Asp Glu Arg Gln Gly Glu Ile Tyr
        675                 680                 685
Val Ala Phe Asn Thr Ser His Leu Pro Ala Val Val Glu Leu Pro Glu
    690                 695                 700
Arg Ala Gly Arg Arg Trp Glu Pro Val Val Asp Thr Gly Lys Pro Ala
705                 710                 715                 720
Pro Tyr Asp Phe Leu Thr Asp Asp Leu Pro Asp Arg Ala Leu Thr Ile
                725                 730                 735
His Gln Phe Ser His Phe Leu Tyr Ser Asn Leu Tyr Pro Met Leu Ser
            740                 745                 750
Tyr Ser Ser Val Ile Leu Val Leu Arg Pro Asp Val
        755                 760
```

<210> SEQ ID NO 4
<211> LENGTH: 24
<212> TYPE: DNA
<213> ORGANISM: Zea mays

<400> SEQUENCE: 4
aaaggcccaa tattatcctt tagg                                          24

<210> SEQ ID NO 5
<211> LENGTH: 31
<212> TYPE: DNA
<213> ORGANISM: Zea mays

<400> SEQUENCE: 5
gccatttcaa ccgttctgaa gtcgggaagt c                                  31

<210> SEQ ID NO 6
<211> LENGTH: 2437
<212> TYPE: DNA
<213> ORGANISM: Triticum aestivum L. cv.Florida
<220> FEATURE:
<221> NAME/KEY: CDS
<222> LOCATION: (16)..(2304)
<223> OTHER INFORMATION:

<400> SEQUENCE: 6

```
gaattcggca cgagg ccg gcg ccg cgc ctg cga cgg tgg cgg ccc aat gcg       51
              Pro Ala Pro Arg Leu Arg Arg Trp Arg Pro Asn Ala
                1               5                   10 acg gcg ggg aag ggg gtc ggc gag gtc tgc gcc gcg gtt gtc gag gtg       99
Thr Ala Gly Lys Gly Val Gly Glu Val Cys Ala Ala Val Val Glu Val
        15                  20                  25 gcg acg aag gcc gag gat gag ggg gag gag gac gag ccg gtg gcg gag      147
Ala Thr Lys Ala Glu Asp Glu Gly Glu Glu Asp Glu Pro Val Ala Glu
    30                  35                  40 gac agg tac gcg ctc ggc ggc gcg tgc agg gtg ctc gcc gga atg ccc      195
Asp Arg Tyr Ala Leu Gly Gly Ala Cys Arg Val Leu Ala Gly Met Pro
45                  50                  55                  60
```

```
acg ccg ctg ggc gcc acc gcg ctc gcc ggc ggg gtc aat ttc gcc gtc      243
Thr Pro Leu Gly Ala Thr Ala Leu Ala Gly Gly Val Asn Phe Ala Val
             65                  70                  75 tac tcc ggc gga gcc aca gcc gcg gcg ctc tgc ctc ttc acg cca gaa      291
Tyr Ser Gly Gly Ala Thr Ala Ala Ala Leu Cys Leu Phe Thr Pro Glu
             80                  85                  90 gat ctc aag gcg gat agg gtg acg gag gag gtt ccc ctt gac ccc ctg      339
Asp Leu Lys Ala Asp Arg Val Thr Glu Glu Val Pro Leu Asp Pro Leu
             95                 100                 105 atg aat cgg act ggg aac gta tgg cat gtc ttc atc gaa ggc gag ctg      387
Met Asn Arg Thr Gly Asn Val Trp His Val Phe Ile Glu Gly Glu Leu
    110                 115                 120 cag gac atg ctt tac ggg tac agg ttc gac ggc acc ttt gct cct cac      435
Gln Asp Met Leu Tyr Gly Tyr Arg Phe Asp Gly Thr Phe Ala Pro His
125                 130                 135                 140 tgc ggg cac tac ctt gat gtt tcc aat gtc gtg gtg gat cct tat gct      483
Cys Gly His Tyr Leu Asp Val Ser Asn Val Val Val Asp Pro Tyr Ala
                145                 150                 155 aag gca gtg ata agc cga ggg gag tat ggt gtt ccg gcg cgt ggt aac      531
Lys Ala Val Ile Ser Arg Gly Glu Tyr Gly Val Pro Ala Arg Gly Asn
            160                 165                 170 aat tgc tgg cct cag atg gct ggc atg atc cct ctt cca tat agc acg      579
Asn Cys Trp Pro Gln Met Ala Gly Met Ile Pro Leu Pro Tyr Ser Thr
        175                 180                 185 ttt gat tgg gaa ggc gac cta cct cta aga tat cct caa aag gac ctg      627
Phe Asp Trp Glu Gly Asp Leu Pro Leu Arg Tyr Pro Gln Lys Asp Leu
    190                 195                 200 gta ata tat gag atg cac ttg cgt gga ttc acg aag cat gat tca agc      675
Val Ile Tyr Glu Met His Leu Arg Gly Phe Thr Lys His Asp Ser Ser
205                 210                 215                 220 aat gta gaa cat ccc ggt act ttc att ggg gct gtg tcg aag ctt gac      723
Asn Val Glu His Pro Gly Thr Phe Ile Gly Ala Val Ser Lys Leu Asp
                225                 230                 235 tat ttg aag gag ctt gga gtt aat tgt att gag tta atg ccc tgc cat      771
Tyr Leu Lys Glu Leu Gly Val Asn Cys Ile Glu Leu Met Pro Cys His
            240                 245                 250 gag ttc aac gag ctg gag tac tca acc tct tct tcc aag atg aac ttt      819
Glu Phe Asn Glu Leu Glu Tyr Ser Thr Ser Ser Ser Lys Met Asn Phe
        255                 260                 265 tgg gga tat tct acc ata aac ttc ttt tca cca atg acg aga tac aca      867
Trp Gly Tyr Ser Thr Ile Asn Phe Phe Ser Pro Met Thr Arg Tyr Thr
    270                 275                 280 tca ggc ggg ata aaa aac tgt ggg cgt gat gcc ata aat gag ttc aaa      915
Ser Gly Gly Ile Lys Asn Cys Gly Arg Asp Ala Ile Asn Glu Phe Lys
285                 290                 295                 300 act ttt gta aga gag gct cac aaa cgg gga att gag gtg atc ctg gat      963
Thr Phe Val Arg Glu Ala His Lys Arg Gly Ile Glu Val Ile Leu Asp
                305                 310                 315 gtt gtc ttc aac cat aca gct gag ggt aat gag aat ggt cca ata tta     1011
Val Val Phe Asn His Thr Ala Glu Gly Asn Glu Asn Gly Pro Ile Leu
            320                 325                 330 tca ttt agg ggg gtc gat aat act aca tac tat atg ctt gca ccc aag     1059
Ser Phe Arg Gly Val Asp Asn Thr Thr Tyr Tyr Met Leu Ala Pro Lys
        335                 340                 345 gga gag ttt tat aac tat tct ggc tgt ggg aat acc ttc aac tgt aat     1107
Gly Glu Phe Tyr Asn Tyr Ser Gly Cys Gly Asn Thr Phe Asn Cys Asn
    350                 355                 360 cat cct gtg gtt cgt caa ttc att gta gat tgt tta aga tac tgg gtg     1155
His Pro Val Val Arg Gln Phe Ile Val Asp Cys Leu Arg Tyr Trp Val
365                 370                 375                 380
```

-continued

| | |
|---|---|
| acg gaa atg cat gtt gat ggt ttt cgt ttt gat ctt gca tcc ata atg<br>Thr Glu Met His Val Asp Gly Phe Arg Phe Asp Leu Ala Ser Ile Met<br>385 390 395 | 1203 |
| acc aga ggt tcc agt ctg tgg gat cca gtt aac gtg tat gga gct cca<br>Thr Arg Gly Ser Ser Leu Trp Asp Pro Val Asn Val Tyr Gly Ala Pro<br>400 405 410 | 1251 |
| ata gaa ggt gac atg atc aca aca ggg aca cct ctt gtt act cca cca<br>Ile Glu Gly Asp Met Ile Thr Thr Gly Thr Pro Leu Val Thr Pro Pro<br>415 420 425 | 1299 |
| ctt att gac atg atc agc aat gac cca att ctt gga ggc gtc aag ctc<br>Leu Ile Asp Met Ile Ser Asn Asp Pro Ile Leu Gly Gly Val Lys Leu<br>430 435 440 | 1347 |
| gtt gct gaa gca tgg gat gca gga ggc ctc tat caa gta ggt caa ttc<br>Val Ala Glu Ala Trp Asp Ala Gly Gly Leu Tyr Gln Val Gly Gln Phe<br>445 450 455 460 | 1395 |
| cct cac tgg aat gtt tgg tct gag tgg aat ggg aag tac cgg gac att<br>Pro His Trp Asn Val Trp Ser Glu Trp Asn Gly Lys Tyr Arg Asp Ile<br>465 470 475 | 1443 |
| gtg cgt caa ttc att aaa ggc act gat gga ttt gct ggt ggt ttt gcc<br>Val Arg Gln Phe Ile Lys Gly Thr Asp Gly Phe Ala Gly Gly Phe Ala<br>480 485 490 | 1491 |
| gaa tgt ctt tgt gga agt cca cac cta tac cag gca gga gga agg aaa<br>Glu Cys Leu Cys Gly Ser Pro His Leu Tyr Gln Ala Gly Gly Arg Lys<br>495 500 505 | 1539 |
| cct tgg cac agt atc aac ttt gta tgt gca cac gat gga ttt aca ctg<br>Pro Trp His Ser Ile Asn Phe Val Cys Ala His Asp Gly Phe Thr Leu<br>510 515 520 | 1587 |
| gct gat ttg gta aca tat aat aac aag tac aat tta cca aat ggg gag<br>Ala Asp Leu Val Thr Tyr Asn Asn Lys Tyr Asn Leu Pro Asn Gly Glu<br>525 530 535 540 | 1635 |
| aac aac aga gat gga gaa aat cac aat ctt agc tgg aat tgt ggg gag<br>Asn Asn Arg Asp Gly Glu Asn His Asn Leu Ser Trp Asn Cys Gly Glu<br>545 550 555 | 1683 |
| gaa gga gaa ttc gca aga ttg tct gtc aaa aga ttg agg aag agg cag<br>Glu Gly Glu Phe Ala Arg Leu Ser Val Lys Arg Leu Arg Lys Arg Gln<br>560 565 570 | 1731 |
| atg cgc aat ttc ttt gtt tgt ctc atg gtt tct caa gga gtt cca atg<br>Met Arg Asn Phe Phe Val Cys Leu Met Val Ser Gln Gly Val Pro Met<br>575 580 585 | 1779 |
| ttc tac atg ggt gat gaa tat ggc cac aca aaa ggg ggc aac aac aat<br>Phe Tyr Met Gly Asp Glu Tyr Gly His Thr Lys Gly Gly Asn Asn Asn<br>590 595 600 | 1827 |
| aca tac tgc cat gat tct tat gtc aat tat ttt cgc tgg gat aaa aaa<br>Thr Tyr Cys His Asp Ser Tyr Val Asn Tyr Phe Arg Trp Asp Lys Lys<br>605 610 615 620 | 1875 |
| gaa caa tac tct gac ttg cac cga ttc tgt tgc ctc atg acc aaa ttc<br>Glu Gln Tyr Ser Asp Leu His Arg Phe Cys Cys Leu Met Thr Lys Phe<br>625 630 635 | 1923 |
| cgc aag gag tgc gag ggt ctt ggc ctt gag gat ttt cca acg gcc gaa<br>Arg Lys Glu Cys Glu Gly Leu Gly Leu Glu Asp Phe Pro Thr Ala Glu<br>640 645 650 | 1971 |
| cgg ctg cag tgg cat ggt cat cag cct ggg aag cct gat tgg tct gag<br>Arg Leu Gln Trp His Gly His Gln Pro Gly Lys Pro Asp Trp Ser Glu<br>655 660 665 | 2019 |
| aat agc cga ttc gtt gcc ttt tcc atg aaa gat gaa aga cag ggc gag<br>Asn Ser Arg Phe Val Ala Phe Ser Met Lys Asp Glu Arg Gln Gly Glu<br>670 675 680 | 2067 |
| atc tat gtg gcc ttc aac acc agc cac tta ccg gcc gtt gtt gag ctc<br>Ile Tyr Val Ala Phe Asn Thr Ser His Leu Pro Ala Val Val Glu Leu<br>685 690 695 700 | 2115 |

| | | | | | | | | | | | | | | | |
|---|---|---|---|---|---|---|---|---|---|---|---|---|---|---|---|
| ccg | gag | cgc | aca | ggg | cgc | cgg | tgg | gaa | ccg | gtg | gtg | gac | aca | ggc | aag | 2163 |
| Pro | Glu | Arg | Thr | Gly | Arg | Arg | Trp | Glu | Pro | Val | Val | Asp | Thr | Gly | Lys | |
| | | | 705 | | | | | 710 | | | | | 715 | | | |
| cca | gca | cca | tac | gac | ttc | ctc | act | gac | gac | tta | cct | gat | cgc | gct | ctc | 2211 |
| Pro | Ala | Pro | Tyr | Asp | Phe | Leu | Thr | Asp | Asp | Leu | Pro | Asp | Arg | Ala | Leu | |
| | | 720 | | | | | 725 | | | | | 730 | | | | |
| acc | ata | cac | cag | ttc | tct | cat | ttc | ctc | aac | tcc | aac | ctc | tac | ccc | atg | 2259 |
| Thr | Ile | His | Gln | Phe | Ser | His | Phe | Leu | Asn | Ser | Asn | Leu | Tyr | Pro | Met | |
| | 735 | | | | | 740 | | | | | 745 | | | | | |
| ctc | agc | tac | tca | tcg | gtc | atc | cta | gta | ttg | cgc | cct | gat | gtt | tga | | 2304 |
| Leu | Ser | Tyr | Ser | Ser | Val | Ile | Leu | Val | Leu | Arg | Pro | Asp | Val | | | |
| 750 | | | | | 755 | | | | | 760 | | | | | | | gaggcggata tacagtaaat aatatgtata tatgtagtcc tttggcgtat tatcagtgtg  2364 cacaattgct ctattgccaa tgatctattc gatccacaga tacatgtgca aaaaaaaaa  2424 aaaaaaactc gag  2437

<210> SEQ ID NO 7
<211> LENGTH: 762
<212> TYPE: PRT
<213> ORGANISM: Triticum aestivum L. cv.Florida

<400> SEQUENCE: 7

Pro Ala Pro Arg Leu Arg Arg Trp Arg Pro Asn Ala Thr Ala Gly Lys
1               5                   10                  15

Gly Val Gly Glu Val Cys Ala Ala Val Val Glu Val Ala Thr Lys Ala
            20                  25                  30

Glu Asp Glu Gly Glu Glu Asp Glu Pro Val Ala Glu Asp Arg Tyr Ala
        35                  40                  45

Leu Gly Gly Ala Cys Arg Val Leu Ala Gly Met Pro Thr Pro Leu Gly
    50                  55                  60

Ala Thr Ala Leu Ala Gly Gly Val Asn Phe Ala Val Tyr Ser Gly Gly
65                  70                  75                  80

Ala Thr Ala Ala Ala Leu Cys Leu Phe Thr Pro Glu Asp Leu Lys Ala
                85                  90                  95

Asp Arg Val Thr Glu Glu Val Pro Leu Asp Pro Leu Met Asn Arg Thr
            100                 105                 110

Gly Asn Val Trp His Val Phe Ile Glu Gly Glu Leu Gln Asp Met Leu
        115                 120                 125

Tyr Gly Tyr Arg Phe Asp Gly Thr Phe Ala Pro His Cys Gly His Tyr
    130                 135                 140

Leu Asp Val Ser Asn Val Val Val Asp Pro Tyr Ala Lys Ala Val Ile
145                 150                 155                 160

Ser Arg Gly Glu Tyr Gly Val Pro Ala Arg Gly Asn Asn Cys Trp Pro
                165                 170                 175

Gln Met Ala Gly Met Ile Pro Leu Pro Tyr Ser Thr Phe Asp Trp Glu
            180                 185                 190

Gly Asp Leu Pro Leu Arg Tyr Pro Gln Lys Asp Leu Val Ile Tyr Glu
        195                 200                 205

Met His Leu Arg Gly Phe Thr Lys His Asp Ser Ser Asn Val Glu His
    210                 215                 220

Pro Gly Thr Phe Ile Gly Ala Val Ser Lys Leu Asp Tyr Leu Lys Glu
225                 230                 235                 240

Leu Gly Val Asn Cys Ile Glu Leu Met Pro Cys His Glu Phe Asn Glu
                245                 250                 255

-continued

```
Leu Glu Tyr Ser Thr Ser Ser Lys Met Asn Phe Trp Gly Tyr Ser
            260                 265                 270

Thr Ile Asn Phe Phe Ser Pro Met Thr Arg Tyr Thr Ser Gly Ile
        275                 280                 285

Lys Asn Cys Gly Arg Asp Ala Ile Asn Glu Phe Lys Thr Phe Val Arg
    290                 295                 300

Glu Ala His Lys Arg Gly Ile Glu Val Ile Leu Asp Val Val Phe Asn
305                 310                 315                 320

His Thr Ala Glu Gly Asn Glu Asn Gly Pro Ile Leu Ser Phe Arg Gly
                325                 330                 335

Val Asp Asn Thr Thr Tyr Tyr Met Leu Ala Pro Lys Gly Glu Phe Tyr
                340                 345                 350

Asn Tyr Ser Gly Cys Gly Asn Thr Phe Asn Cys Asn His Pro Val Val
            355                 360                 365

Arg Gln Phe Ile Val Asp Cys Leu Arg Tyr Trp Val Thr Glu Met His
    370                 375                 380

Val Asp Gly Phe Arg Phe Asp Leu Ala Ser Ile Met Thr Arg Gly Ser
385                 390                 395                 400

Ser Leu Trp Asp Pro Val Asn Val Tyr Gly Ala Pro Ile Glu Gly Asp
                405                 410                 415

Met Ile Thr Thr Gly Thr Pro Leu Val Thr Pro Pro Leu Ile Asp Met
                420                 425                 430

Ile Ser Asn Asp Pro Ile Leu Gly Gly Val Lys Leu Val Ala Glu Ala
            435                 440                 445

Trp Asp Ala Gly Gly Leu Tyr Gln Val Gly Gln Phe Pro His Trp Asn
    450                 455                 460

Val Trp Ser Glu Trp Asn Gly Lys Tyr Arg Asp Ile Val Arg Gln Phe
465                 470                 475                 480

Ile Lys Gly Thr Asp Gly Phe Ala Gly Gly Phe Ala Glu Cys Leu Cys
                485                 490                 495

Gly Ser Pro His Leu Tyr Gln Ala Gly Gly Arg Lys Pro Trp His Ser
            500                 505                 510

Ile Asn Phe Val Cys Ala His Asp Gly Phe Thr Leu Ala Asp Leu Val
    515                 520                 525

Thr Tyr Asn Asn Lys Tyr Asn Leu Pro Asn Gly Glu Asn Asn Arg Asp
530                 535                 540

Gly Glu Asn His Asn Leu Ser Trp Asn Cys Gly Glu Glu Gly Glu Phe
545                 550                 555                 560

Ala Arg Leu Ser Val Lys Arg Leu Arg Lys Arg Gln Met Arg Asn Phe
                565                 570                 575

Phe Val Cys Leu Met Val Ser Gln Gly Val Pro Met Phe Tyr Met Gly
            580                 585                 590

Asp Glu Tyr Gly His Thr Lys Gly Gly Asn Asn Asn Thr Tyr Cys His
    595                 600                 605

Asp Ser Tyr Val Asn Tyr Phe Arg Trp Asp Lys Lys Glu Gln Tyr Ser
    610                 615                 620

Asp Leu His Arg Phe Cys Cys Leu Met Thr Lys Phe Arg Lys Glu Cys
625                 630                 635                 640

Glu Gly Leu Gly Leu Glu Asp Phe Pro Thr Ala Glu Arg Leu Gln Trp
                645                 650                 655

His Gly His Gln Pro Gly Lys Pro Asp Trp Ser Glu Asn Ser Arg Phe
                660                 665                 670
```

-continued

```
Val Ala Phe Ser Met Lys Asp Glu Arg Gln Gly Glu Ile Tyr Val Ala
        675                 680                 685

Phe Asn Thr Ser His Leu Pro Ala Val Val Glu Leu Pro Glu Arg Thr
        690                 695                 700

Gly Arg Arg Trp Glu Pro Val Val Asp Thr Gly Lys Pro Ala Pro Tyr
705                 710                 715                 720

Asp Phe Leu Thr Asp Asp Leu Pro Asp Arg Ala Leu Thr Ile His Gln
                725                 730                 735

Phe Ser His Phe Leu Asn Ser Asn Leu Tyr Pro Met Leu Ser Tyr Ser
            740                 745                 750

Ser Val Ile Leu Val Leu Arg Pro Asp Val
        755                 760

<210> SEQ ID NO 8
<211> LENGTH: 20
<212> TYPE: DNA
<213> ORGANISM: Triticum asetivum L. cvFlorida

<400> SEQUENCE: 8
gctttacggg tacaggttcg                                              20

<210> SEQ ID NO 9
<211> LENGTH: 18
<212> TYPE: DNA
<213> ORGANISM: Triticum asetivum L. cvFlorida

<400> SEQUENCE: 9
gctttacggg tacaggtt                                                18

<210> SEQ ID NO 10
<211> LENGTH: 51
<212> TYPE: DNA
<213> ORGANISM: Triticum asetivum L. cvFlorida

<400> SEQUENCE: 10
gcggtacctc tagaaggaga tatacatatg gcggaggaca ggtacgcgct c            51

<210> SEQ ID NO 11
<211> LENGTH: 33
<212> TYPE: DNA
<213> ORGANISM: Triticum asetivum L. cvFlorida

<400> SEQUENCE: 11
gctcgagtcg actcaaacat cagggcgcaa tac                               33
```

NUCLEIC ACID MOLECULES WHICH CODE FOR ENZYMES DERIVED FROM WHEAT AND WHICH ARE INVOLVED IN THE SYNTHESIS OF STARCH

CROSS-REFERENCE TO RELATED APPLICATIONS

This application claims the benefit of and priority to PCT Applications PCT/EP99/03141 filed May 07, 1999 and DE 198 20608.9 filed May 08, 1998.

STATEMENT REGARDING FEDERALLY SPONSORED RESEARCH AND DEVELOPMENT

Not applicable.

BACKGROUND OF THE INVENTION

The present invention relates to nucleic acid molecules which encode a wheat enzyme involved in starch synthesis in plants. This enzyme is an isoamylase.

The invention furthermore relates to vectors, host cells, plant cells and plants comprising the nucleic add molecules according to the invention.

Furthermore, there are described methods for the generation of transgenic plants which, owing to the introduction of nucleic acid molecules according to the invention, synthesize starch with altered characteristics.

In view of the increasing importance attributed lately to plant constituents as renewable raw materials, one of the objects of biotechnology research addresses the adaptation of these plant raw materials to the needs of the processing industries. Moreover, to allow renewable raw materials to be used in as many fields as possible, a wide diversity of materials must be generated.

Apart from oils, fats and proteins, polysaccharides constitute the important renewable raw materials from plants. Apart from cellulose, starch—which is one of the most important storage substances in higher plants—takes a central position amongst the polysaccharides. In this context, wheat is one of the most important crop plants since it provides approximately 20% of the total starch production in the European Community.

The polysaccharide starch is a polymer of chemically uniform units, the glucose molecules. However, it is a highly complex mixture of different molecule types which differ with regard to their degree of polymerization, the occurrence of branching of the glucose chains and their chain lengths, which, in addition, may be derivatized, for example phosphorylated. Starch therefore does not constitute a uniform raw material. In particular, a distinction is made between amylose starch, an essentially unbranched polymer of alpha-1,4-glycosidically linked glucose molecules, and amylopectin starch, which, in turn, constitutes a complex mixture of glucose chains with various branchings. The branchings occur by the occurrence of additional alpha-1,6-glycosidic linkages. In wheat, amylose starch makes up approximately 11 to 37% of the starch synthesized.

To allow suitable starches to used in the widest possible manner for the widest possible range of industrial needs, it is desirable to provide plants which are capable of synthesizing modified starches which are particularly well suited to various purposes. One possibility of providing such plants is to employ plant-breeding measures. However, since wheat is polyploid in character (tetra- and hexaploid), the exertion of influence by plant breeding proves to be very difficult. A "Waxy" (amylose-free) wheat was generated only recently by crossing naturally occurring mutants (Nakamura et al., Mol. Gen. Genet. 248 (1995), 253–259).

An alternative to plant-breeding methods is the specific modification of starch-producing plants by recomtbinant methods. However, prerequisites are the identification and characterization of the enzymes which are involved in starch synthsis and/or starch modification and the isolation of the nucleic acid molecules encoding these enzymes.

The biochemical pathways which lead to the synthesis of starch are essentially known. Starch synthesis in plant cells takes place in the plastids. In photosynthetically active tissue, these plastids are the chloroplasts and in photosynthetically inactive, starch-storing tissue are amyloplasts.

A further specific alteration of the degree of branching of starch synthesized in plants with the aid of recombinat methods still requires identification of DNA sequences, which encode enzymes involved in starch metabolism, in particular in the introduction or degradation of branching within the starch molecules.

Besides the so-called Q enzymes, which introduce branchings into starch molecules, enzymes occur in plants which are capable of breaking down branchings. These enzymes are called debranching enzymes and, according to their substrate specificity, they are divided into three groups:

(a) The pullulanases, which, in addition to pullulan, also utilize amylopectin as substrate, are found in microorganisms, for example *Klebsiella* and in plants. In plants, these enzymes are also termed R enzymes.

(b) The isoamylases, which do not utilize pullulan, but indeed glycogen and amylopectin as substrate, are also found in microorganisms and plants. For example, isoamylases have been described in maize (Manners & Carbohydr. Res. 9 (1969), 107) and potato (Ishizaki et al., Agric. Biol. Chem. 47 (1983), 771–779).

(c) The amylo-1,6glucosidases are described in mammals and yeasts and utilize grenzdextrins as substrate.

In sugar beet, Li et al. (Plant Physiol. 98 (1992), 1277–1284) were only able to find one debranching enzyme of the pullulanase type, in addition to five endoamylases and two exoamylases. This enzyme, which has a size of approx. 100 kD and a pH optimum of 5.5, is localized in the chloroplasts. In spinach, too, a debranching enzyme was described which utilizes pullulan as substrate. The activity both of the spinach debranching enzyme and of the sugar beet debranching enzyme upon reaction with amylopectin as substrate is five times lower in comparison with pullulan as substrat (Ludwig et al., Plant Physiol. 74 (1984), 856–861; Li et al., Plant Physiol. 98 (1992), 1277–1284).

In the agronomically important starch-storing crop plant potato, the activity of a debranching enzyme was studied by Hobson et al. (J. Chem. Soc., (1951), 1451). It was proved successfully that, in contrast to the Q enzyme, this enzyme has no chain-extending activity, but merely hydrolyzes alpha-1,6-glycosidic bonds. However, it has been impossible as yet to characterize the enzyme in greater detail. In the case of potatoes, processes for purifying the debranching enzyme and partial peptide sequences of the purified protein have already been proposed (WO 95/04826). In the case of spinach, the purification of a debranching enzyme and the isolation of suitable cDNA have been described in the meantime (Renz et al., Plant Physiol. 108 (1995), 1342).

In maize, only the existence of one debranching enzyme has been described as yet in the literature. Owing to its substrate specificity, this enzyme is classified as belonging to the group of the isoamylases (see, for example, Hannah et al., Scientia Horticulturae 55 (1993), 177–197 or Garwood (1994) in Starch Chemistry and Technology, Whistler, R. L, BeMiller, J. N., Puschafl, E. F. (eds.), Academic Press San Diego, New York, Boston, 25–86). The corresponding mutant is termed "sugary". The gene of the sugary locus has been cloned recently (see James et al., Plant C II 7 (1995), 417–429). Apart from the sugary locus, no other gene locus which encodes a protein with debranching enzyme activity is as yet known in maize. Also, there have been no indications to date that other debranching enzyme forms occur in maize. If transgenic maize plants are to be generated which no longer have any debranching enzyme activities whatsoever, for example in order to extend the degree of branching of the amylopectin starch, it is necessary to identify all debranching enzymes forms which occur in maize and to isolate the corresponding genes or cDNA sequences.

To provide further possibilities of altering any starch-storing plant, preferably cereals, in particular wheat, so that it synthesizes a modified starch, it is necessary to identify in each case DNA sequences which encode further isoforms of branching enzymes.

BRIEF SUMMARY OF THE INVENTION

The object of the present invention is therefore to provide nucleic acid molecules encoding enzymes involved in starch synthesis, which allow genetically modified plants to be generated which make possible the production of plant starches whose chemical and/or physical characteristics are altered.

This object is achieved by providing the use forms designated in the patent claims.

DETAILED DESCRIPTION OF THE INVENTION

The present invention therefore relates to a nucleic acid molecule which encodes a protein with the function of a wheat isoamylase, preferably a protein which is essentially defined by the amino acid sequence stated under Seq ID No. 3 or 7. In particular, the invention relates to a nucleic acid molecule comprising the nucleotide sequence stated under Seq ID No. 1, 2 or 6, or a part thereof, preferably a molecule comprising the coding region stated in Seq ID No. 1, 2 or 6, and corresponding ribonucleotide sequences. Very especially preferred is a nucleic acid molecule furthermore comprising regulatory elements which ensure transcription and, if appropriate, translation of said nucleic acid molecules. The subject matter of the invention is furthermore a nucleic acid molecule which hybridizes with one of the nucleic acid molecules according to the invention.

The subject matter of the invention is also a nucleic acid molecule encoding a wheat isoamylase whose sequence deviates from the nucleotide sequences of the above-described molecules owing to the degeneracy of the genetic code.

The invention also relates to a nucleic acid molecule with a sequence which is complementary to all or part of one of the abovementioned sequences.

The term "hybridization" as used in the context of the present invention denotes hybridization under conventional hybridization conditions, preferably under stringent conditions, as they are described, for example, by Sambrook et al., Molecular Cloning, A Laboratory Manual, 2nd Ed. (1989) Cold Spring Harbor Laboratory Press, Cold Spring Harbor, N.Y.).

"Hybridization" especially preferably takes place under the following conditions:

| | |
|---|---|
| Hybridization buffer: | 2 × SSC; 10 × Denhardt solution (Fikoll 400 + PEG + BSA; ratio 1:1:1); 0.1% SDS; 5 mM EDTA; 50 mM $Na_2HPO_4$; 250 µg/ml Herring sperm DNA; 50 µg/ml tRNA; or 0.25 M sodium phosphate buffer pH 7.2; 1 mM EDTA; 7% SDS |
| Hybridization temperature | T = 65 to 70° C. |
| Wash buffer: | 0.2 × SSC; 0.1% SDS |
| Wash temperature | T = 40 to 75° C. |

Nucleic acid molecules which hybridize with the nucleic acid molecules according to the invention are capable, in principle, of encoding isoamylases from any wheat plant which expresses such proteins.

Nucleic acid molecules which hybridize with the molecules according to the invention can be isolated for example from genomic libraries or cDNA libraries of wheat or wheat plant tissue. Alternatively, they can be generated by recombinant methods or synthesized chemically.

Identification and isolation of such nucleic acid molecules can be effected using the molecules according to the invention or parts of these molecules or the reverse complements of these molecules, for example by means of hybridization by standard methods (see, for example, Sambrook et a., 1989, Molecular Cloning, A Laboratory Manual, 2nd Ed. Cold Spring Harbor Laboratory Press, Cold Spring Harbor, N.Y.).

Hybridization probes which can be used are, for example, nucleic acid molecules which have exactly ore essentially the nucleotide sequence stated under SEQ ID NOs: 1, 2 or 6 or parts of these sequences. The fragments used as hybridization probes may also be synthetic fragments which have been prepared with the aid of the customary synthetic techniques whose sequence essentially agrees with that of a nucleic acid molecule according to the invention.

The molecules hybridizing with the nucleic acid molecules according to the invention also encompass fragments, derivatives and allelic variants of the above-described nucleic acid molecules which encode a wheat isoamylase according to the invention. Fragments are to be understood as meaning parts of the nucleic acid molecules of sufficient length so as to encode one of the proteins described. The term derivative means in this context that the sequences of these molecules differ from the sequences of the above-described nucleic acid molecules at one or more positions and have a high degree of homology with these sequences. Homology means a sequence identity of at least 40%, in particular of at least 60%, preferably over 80%, especially preferably over 90%. The deviations relative to the above described nucleic acid molecules may have been generated by deletion, substitution, insertion or recombination.

Homology furthermore means that functional and/or structural equivalence exists between the nucleic acid molecules in question or the proteins encoded by them. The nucleic acid molecules which are homologous to the above-described molecules and constitute derivatives of these molecules are, as a rule, variations of these molecules which constitute modifications exerting the same biological function. They may be naturally occurring variations, for example, sequences from other organisms, or mutations which may have occurred naturally or been introduced by directed mutagenesis. Furthermore, the variations may be synthetically generated sequences. The allelic variants may be both naturally occurring variants and synthetically generated variants or variants produced by recombinant DNA techniques.

The isoamylases encoded by the various variants of the nucleic acid molecules according to the invention share certain characteristics. These may include, for example, enzyme activity, molecular weight. immunological reactivity, conformation and the like, or else physical properties such as, for example, the migration behavior in gelelectrophoresis, the chromatographic behavior, sedimentation coefficients, solubility, spectroscopic characteristics, charge characteristics, stability; pH optimum, temperature optimum and the like.

The protein encoded by the nucleic acid molecules according to the invention is a wheat isoamylase. These proteins show certain homology ranges with isoamylases from other plant species which are already known.

The nucleic acid molecules according to the invention may be DNA molecules, in particular cDNA or genomic molecules. Furthermore, the nucleic acid molecules according to the invention may be RNA molecules which may result, for example, from the transcription of a nucleic acid molecule according to the invention. The nulcleic acid molecules according to the invention may have been obtained, for example, from natural sources or they may have been generated by recombinant techniques or synthesized.

Subject matter of the invention are also oligonucleotides which hybridize specifically with a nucleic acid molecule according to the invention. Such oligonucleotides preferably have a length of at least 10, in particular of at least 15 and especially preferably of at least 50 nucleotides. The oligonucleotides according to the invention hybridize specifically with nucleic acid molecules according to the invention, i.e. not or only to a very low degree with nucleic acid sequences which encode other proteins, in particular other isoamylases. The oligonucleotides according to the invention can be used, for example, as primers for a PCR reaction or as hybridization probe for the isolation of the related genes. Equally, they may be constituents of antisense constructs or of DNA molecules encoding suitable ribozymes.

The invention furthermore relates to vectors, in particular plasmids, cosmids, phagemids, viruses, bacteriophages and other vectors conventionally used in genetic engineering comprising the above-described nucleic acid molecules according to the invention. Such vectors are suitable for the transformation of pro- or eukaryotic cells, preferably plant cells.

The vectors especially preferably permit integration of the nucleic acid molecules according to the invention, if appropriate together with flanking regulatory regions, into the genome of the plant cell. Examples are binary vectors which can be employed in agrobacterial-mediated gene transfer. Preferably, integration of a nucleic acid molecule according to the invention in sense or antisense orientation ensures that a translatable or, if appropriate, nontranslatable RNA is synthesized in the transformed pro- or eukaryotic cells.

The term "vector" generally denotes a suitable auxiliary known to the skilled worker which allows the directed transfer of a single- or double-stranded nucleic acid molecule into a host cell, for example a DNA or RNA virus, a virus fragment, a plasmid construct which, in the absence or presence of regulatory elements, may be suitable for transferring nucleic acid into cells, or support materials such as glass fibers or else metal particles as can be employed, for example, in the particle gun method, but it may also encompass a nucleic acid molecule which can be introduced directly into a cell by means of chemical or physical methods.

In a preferred embodiment, the nucleic acid molecules within the vectors are linked to regulatory elements which ensure transcription and synthesis of a translatable RNA in pro- or eukaryotic cells or which—if desired—ensure synthesis of a nontranslatable RNA.

Expression of the nucleic add molecules according to the invention in prokaryotic cells, for example, in *Escherichia coil*, is of importance for a more detailed characterization of the enzymatic activities of the enzymes encoded by these molecules. In particular, it is possible to characterize the product synthesized by the enzymes in question in the absence of other enzymes involved in starch synthesis in the plant cell. This permits conclusions to be drawn regarding the function which the protein in question exerts during starch synthesis in the plant cell.

In addition, various types of mutations can be introduced into the nucleic acid molecules according to the invention by means of customary techniques of molecular biology (see, tor example, Sambrook et al., 1989, Molecular Cloning, A Laboratory Manual, 2nd Ed. Cold Spring Harbor Laboratory Press, Cold Spring Harbor, N.Y.), resulting in the synthesis of proteins whose biological properties may be altered. Possible here is, on the one hand, the generation of deletion mutants in which nucleic acid molecules are generated by successive deletions from the 5' or the 3' end of the coding DNA sequence which lead to the synthesis of correspondingly truncated proteins. Such deletions at the 5' end of the nucdeotide sequence allow, for example, amino acid sequences to be identified which are responsible for translocation of the enzyme into the plastids (transit peptides). This allows the directed generation of enzymes which, owing to the removal of the sequences in question, are no longer localized in the plastids, but in the cytosol, or which, owing to the addition of other signal sequences, are localized in other compartments.

On the other hand, it is also possible to introduce point mutations at positions where an altered amino acid sequence affects, for example, enzyme activity or enzyme regulation. In this manner, it is possible to generate, for example, mutants which have an altered $K_m$ value or which are no longer subject to the regulatory mechanisms via allosteric regulation or covalent modification which are normally present in the cell.

Furthermore, it is possible to generate mutants which have an altered substrate or product specificity of the protein according to the invention. Furthermore, it is possible to generate mutants which have an altered activity-temperature profile of the protein according to the invention.

To carry out the recombinant modification of prokaryotic cells, the nucleic acid molecules according to the invention or parts of these molecules can be introduced into plasmids which allow mutagenesis to take place or a sequence to be altered by recombining DNA sequences. Base exchanges can be carried out or natural or synthetic sequences added with the aid of standard methods (cf. Sambrook et al., 1989, Molecular Cloning: A laboratory manual, 2nd Ed., Cold Spring Harbor Laboratory Press, N.Y., USA). To link the DNA fragments to each other, adapters or linkers may be attached to the fragments. Furthermore, manipulations may be employed which provide suitable restriction cleavage sites or which eliminate superfluous DNA or restriction cleavag sites. Where insertions, deletions or substitutions are suitable, in vitro mutage nesis, primer repair, restriction or ligation may be employed. Analytical methods which are generally employed are sequence analysis, restriction analysis or other methods of biochemistry and molecular biology.

In a further embodiment, the invention relates to host cells, in particular pro- or eukaryotic cells, which have been transformed with an above-described nucleic acid molecule according to the invention or a vector according to the invention, and to cells which are derived from cells transformed thus and comprise a nucleic acid molecule according to the invention or a vector. They are preferably pro or eukaryotic cells, in particular plant cells.

Subject matter of the invention are furthermore proteins with isoamylase activity which are encoded by the nucleic acid molecules according to the invention and which can be prepared by recombinant technology, and processes for their preparation, where a host cell according to the invention is cultured under suitable conditions which are known to the skilled worker and which permit synthesis of the protein according to the invention and it is subsequently isolated from the host cells and/or the culture medium.

Providing the nucleic acid molecules according to the invention now makes it possible to intervene, with the aid of recombinant methods, in a directed fashion in the starch metabolism of plants and to alter it so that the resultant synthesis is of modified starch whose physicochemical properties, for example the amyloselamylopectin ratio, the degree of branching, the average chain length, the phosphate content, the gelatinization behavior, the gel- or film-forming properties, the starch granule size and/or the starch granule shape is altered in comparison to known starch.

Thus, it is possible to express the nucleic acid molecules according to the invention in plant cells in order to increase the activity of the isoamylase in question, or to introduce them into cells which do not naturally express this enzyme. Expressing the nucleic acid molecules according to the invention also makes it possible to lower the natural activity level of the isoamylase according to the invention in the plant cells. Furthermore, it is possible to modify the nucleic acid molecules according to the invention by methods known to the skilled worker in order to obtain isoamylases according to the invention which are no longer subject to the cell's intrinsic regulatory mechanism or which have altered temperature-activity profiles or substrate or product specificities.

When expressing the nucleic acid molecules according to the invention in plants, it is possible, in principle, for the protein synthesized to be localized in any desired compartment of the plant cell. To achieve localization in a particular compartment, the sequence ensuring localization in plastids must be deleted and the remaining encoding region must, if necessary, be linked to DNA sequences which ensure localization in the compartment in question. Such sequences are known (see, for example, Braun et al., EMBO J. 11 (1992), 3219–3227; Wofter et al., Proc. Natl., Acad. Sci. USA 85 (1988), 846–850; Sonnewald et al., Plant J. 1 (1991), 95–106).

The present invention thus also relates to a method for generating transgenic plant cells which have been transformed with a nucleic acid molecule or a vector according to the invention, where a nucleic acid molecule according to the invention or a vector according to the invention is integrated into the genome of a plant cell, the transgenic plant cells which have been transformed by means of a vector or nucleic acid molecule according to the invention, and transgenic plant cells derived from cells transformed thus. The cells according to the invention comprise one or more nucleic acid molecules or vectors according to the invention, these preferably being linked to regulatory DNA elements which ensure transcription in plant cells, in particular to a suitable promoter. Such cells can be distinguished from naturally occurring plant cells inter alia by the fact that they comprise a nucleic acid molecule according to the invention which does not occur naturally in these cells, or by the fact that such a molecule exists integrated at a location in the cell's genome where it does not occur otherwise, i.e. in a different genomic environment. Furthermore, such transgenic plant cells according to the invention can be distinguished from naturally occurring plant cells by the fact that they comprise at least one copy of a nucleic add molecule according to the invention stably integrated into the genome, if appropriate in addition to the copies of such a molecule which occur naturally in the cells. If the nucleic acid molecule(s) introduce into the cells is(are) additional copies to molecules which already occur naturally in the cells, then the plant cells according to the invention can be distinguished from naturally occurring plant cells in particular by the fact that this additional copy, or these additional copies, is, or are, localized at locations in the genome where it does not occur naturally, or they do not occur naturally. This can be checked, for example, with the aid of a Southern blot analysis.

If the nucleic acid molecule according to the invention which has been introduced into the plant genome is heterologous to the plant cell, the transgenic plant cells exhibit transcripts of the nucleic acid molecules according to the invention which can be detected in a simple manner by methods known to the skalled worker, for example by Northem blot analysis.

If the nucleic acid molecule according to the invention which has been introduced is homologous to the plant cell, the cells according to the invention can be distinguished from naturally occurring cells, for example, on the basis of the additional expression of nucleic acid molecules according to the invention. The transgenic plant cells preferably comprise more transcripts of the nucleic acid molecules according to the invention. This can be detected, for example, by Northem blot analysis. "More" in this context means preferably at least 10% more, preferably at least 20% more, especially preferably at least 50% more transcripts than corresponding untransformed cells. The cells furthermore preferably exhibit a corresponding increase or decrease in the activity of the protein according to the invention (at least 10%, 20% or 50%). The transgenic plant cells can be regenerated into intact plants by techniques known to the skilled worker.

Another subject matter of the present invention is a method for the generation of transgenic plants, where one or more nucleic acid molecules or vectors according to the invention are integrated into the genome of a plant cell and a complete plant is regenerated from said plant cell. Subject matter of the invention are furthermore plants which comprise the above-described transgenic plant cells. In principle, the transgenic plants can be plants of any species, i.e. not only monocotyledonous but also dicotyledonous plants. They are preferably useful plants, by preference starch-synthesizing or starch-storing plants, especially preferably rye, barley oats, wheat, sorghum and millet, sago, maize, rice, peas, marrowfat peas, cassava, potatoes, tomatoes, oilseed rape, soybeans, hemp, flax, sunflowers, cowpeas or arrowroot, in particular wheat, maize, rice and potatoes.

The invention also relates to propagation material of the plants according to the invention, for example fruits, seeds, tubers, rootstocks, seedlings, cuttings, calli, protoplasts, cell cultures and the like.

The present invention furthermore relates to a process for the preparation of a modified starch comprising the step of extracting the starch from an above-described plant according to the invention and/or starch-storing parts of such a plant.

Processes for extracting the starch from plants or starch-storing parts of plants, in particular from wheat, are known to the skilled worker, cf., for example, Eckhoff et al. (Cereal Chem. 73 (1996) 54–57) "Starch: Chemistry and Technology (Eds.: Whistler, BeMiller and Paschall (1994), 2nd Edition, Academic Press Inc. London Ltd; ISBN 0-12-746270-8; see, for example, Chapter XII, pages 412–468: Corn and sorghum starches: production; by Watson; Chapter XIII, pages 469–479; Tapioca, arrowroot and sago starches: production; by Corbishley and Miller; Chapter XIV, pages 479–490: Potato starch: production and uses; by Mitch; Chapter XV, pages 491 to 506: Wheat starch: production, modification and uses; by Knight and Oson; and Chapter XVI, pages 507 to 528: Rice starch: production and uses; by Rohmer and Klem). Devices normally used in processes for extracting starch from plant material are separators, decanters, hydrocyclones, spray dryers and fluidizeded-bed dryers.

Owing to the expression of a nucleic acid molecule according to the invention, the transgenic plant cells and plants according to the invention synthesize a starch whose physicochemical properties, for example th amylose/amylopectin ratio, the degree of branching, the average chain length, the phosphate content, the gelatinization behavior, the starch granule size and/or starch granule shape is altered compared with starch synthesized in wild-type plants. In particular, such a starch may be altered with regard to viscosity and/or the film- or gel-forming properties of gels made from this starch in comparison with known starches.

Subject matter of the present invention is furthermore a starch which is obtainable from the plant cells and plants according to the invention and their propagation material and starch which is obtainable by the above-described process according to the invention.

It is furthermore possible to generate, with the aid of the nucleic acid molecules according to the invention, plant cells and plants in which the activity of a prot in according to the invention is reduced. This also leads to the synthesis of a starch with altered chemical and/or physical characteristics compared with starch from wild-type plant cells.

A further subject matter of the invention is thus also a transgenic plant cell comprising a nucleic acid molecule according to the invention in which the activity of an isoamylase is reduced in comparison with untransformed cells.

Plant cells with a reduced activity of an isoamylase can be obtained, for example, by expressing a suitable antisense RNA, a sense RNA for achieving a cosuppression effect or by expressing a suitably constructed ribozyme which specifically cleaves transcripts which encode an isoarnylase, making use of the nucleic acid molecules according to the invention by methods known to the skilled worker, cf. Jorgensen (Trends Biotechnol. 8 (1990), 340–344), Niebel et al., (Curr. Top. Microbiol. Immunol. 197 (1995). 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621).

To reduce the activity of an isoamylase according to the invention, it is preferred to reduce, in the plant cells, the number of transcripts encoding it, for example by expressing an antisense RNA.

Here, it is possible to make use, on the one hand, of a DNA molecule which encompasses all of the sequence encoding a protein according to the invention, inclusive of any flanking sequences which may be present, or else of DNA molecules which only encompass parts of the cooling sequence, it being necessary for these parts to be sufficiently long so as to cause an anfisense effect in the cells. In general, sequences up to a minimum length of 15 bp, preferably with a length of 100–500 bp, may be used for efficient antisense inhibition in particular sequences with a length of over 500 bp. As a rule, DNA molecules are used which are shorter than 5000 bp, preferably sequences which are shorter than 2500 bp.

Also possible is the use of DNA sequences which show a high degree of homology with the sequences of the DNA molecules according to the invention, but are not completely identical. The minimum homology should exceed approx. 65%. The use of sequences with homologies between 95 and 100% is to be preferred.

Subject matter of the invention is also a process for producing a modified starch encompassing the step of extracting the starch from a cell or plant according to the invention and/or from starch-storing parts of such a plant.

Subject matter of the invention is furthermore starch which can be obtained from the cells or plants according to the invention and their propagation material or parts, and also starch which can be obtained by a process according to the invention.

The starches according to the invention can be modified by methods known to the skilled worker and are suitable, in their unmodified or modified form, for a variety of applications in the food or non-food sectors.

In principle, the possible uses of the starches according to the invention can be divided into two important sectors. One sector encompasses the hydroyzates of the starch, mainly glucose and glucan units, which are obtained by enzymatic or chemical methods. They are used as starting material for further chemical modifications and processes such as fermentation. What would be feasible for reducing the costs is the simplicity and economic design of a hydrolytic method. It currently proceeds essentiaily enzymatically using amyloglucosidase. What would be feasible is a financial saving by using less enzyme. This could be caused by altering the structure of the starch, for example by increasing the surface area of the granule, better digestibility, for example owing to a lower degree of branching or a sterical structure which limits the accessibility for the enzymes employed.

The other sector in which the starch according to the invention can be used as so-called native starch, owing to its polymeric structure, can be divided into two further fields of application:

1. The food industry

Starch is a traditional additive to a large number of foodstuffs in which its function is essentially to bind aqueous additives or to cause increased viscosity or else increased gelling. Important characteristics are the rheology, the sorptive characteristics, the swelling temperature, the gelatinization temperature, the viscosity, the thickening power, the starch solubility, the transparency and gel structure, the thermal stability, the shear stability, the stability to acids, the tendency to undergo retrogradation, the film-forming capacity, the freeze-thaw stability, the viscosity stability in salt solutions, the digestibility and the ability to form complexes with, for example, inorganic or organic ions.

2. The non-food industry

In this large sector, starch can be employed as auxiliary for various preparation processes or as an additive in industrial products. When using starch as an auxiliary, mention must be made, in particular, of the paper and board industry. Starch acts mainly for retardation purposes (retaining solids), for binding filler particles and fines, as stiffener and for dehydration. Moreover, the advantageous properties of starch regarding stiffness, strength, sound, touch, luster, smoothness, bonding strength and the surfaces is utilized.

2.1 Paper and board industry

Within the papermaking process, four fields of application must be distinguished, i.e. surface, coating, stock and spraying. The demands on starch with regard to surface treatment are essentially high whiteness, an adapted viscosity, high viscosity stability, good film formation and low dust formation. When used for coating, the solids content, a suitable viscosity, a high binding capacity and a high pigment affinity play an important role. Of importance when used as additive to the stock is rapid, uniform, loss-free distribution, high mechanical strength and complete retention in the paper web. If the starch is used in the spraying sector, again, an adapted solids content, high viscosity and high binding capacity are of importance.

2.2 The adhesives industry

An important field of application for starches is the adhesives industry, where the potential uses can be divided into four subsections: the use as a pure starch paste, the use in starch pastes which have been treated with specialty chemicals, the use of starch as additiv to synthetic resins and polymer dispersions, and the use of starches as extenders for synthetic adhesives. 90% of the starch-based adhesives are employed in the sectors production of corrugated board, production of paper sacks and bags, production of composite materials for paper and aluminum, production of boxes and gumming adhesives for envelopes, stamps and the like.

2.3 Textile industry and textile care products industry

An important field of application for starches as auxiliaries and additives is the sector production of textiles and textile care products. The following four fields of application must be distinguished within the textile industry: the use of starch as sizing agent, i.e. as auxiliary for smoothing and strengthening the smoothing behavior as protection from the tensile forces applied during weaving, and for increasing abrasion resistance during weaving, starch as a textile finishing agent, in particular after quality-reducing pretreatments such as bleaching, dyeing and the like, starch as thickener in the preparation of dye pastes for preventing bleeding, and starch as additive to glazing agents for sewing threads.

2.4 Construction materials industry

The fourth field of application is the use of starches as additives in construction materials. An example is the production of gypsum plasterboards, where the starch which is admixed to the gypsum slurry gelatinizes with the water, diffuses to the surface of the plaster core and there binds the board to the core. Other fields of application are the admixture to rendering and mineral fibers. In the case of ready-mixed concrete, starch products are employed for delaying binding.

2.5 Soil stabilization

Another market for starch products is the production of soil stabilizers, which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6 Use in crop protection products and fertilizers

One field of application for using starch is in crop protection products for altering the specific properties of the products. Thus, starch can be employed for improving the wettability of crop protection products and fertilizers, for the controlled release of the active ingredients, for converting liquid, volatile and/or malodorous active ingredients into microcrystalline, stable, shapeable substances, for mixing incompatible compounds and for extending the duration of action by reducing decomposition.

2.7 Pharmaceuticals, medicine and cosmetics industry

Another field of application is the sector of the pharmaceuticals, medicine and cosmetics industry. In the pharmaceuticals industry, starch can be employed as binder for tablets or for diluting the binder in capsules. Moreover, starch can be employed as tablet disintegrant since it absorbs fluid after swallowing and swells within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8 Addition of starch to coal and briquettes

A field of application for starch is as additive to coal and briquettes. With an addition of starch, coal can be agglomerated, or briquetted, in terms of high quantity, thus preventing premature decomposition of the briquettes. In case of barbecue coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9 Ore slick and coal silt processing

Furthermore, starch can be employed as flocculant in the ore slick and coal silt processing sector.

2.10 Foundry auxiliary

A further field of application is as additive to foundry auxiliaries. Various casting processes require cores made with sands treated with binders. The binder which is predominantly employed nowadays is bentonite, which is treated with modified starches, in most cases swellable starches. The purpose of adding starch is to increase flowability and to improve the binding power. In addition, the swellable starches can meet other demands of production engineering, such as being cold-water-dispersible, rehydratable, readily miscible with sand and having high water-binding capacity.

2.11 Use in the rubber industry

In the rubber industry, starch is employed for improving the technical and visual quality. The reasons are the improvement of the surface luster, the improvement of handle and of appearance, and to this end starch is scattered on to the tacky gummed surface of rubber materials prior to cold curing, and also the improvement of the rubber's printability.

2.12 Production of leather substitutes

Modified starches may furthermore also be sold for the production of leather substitutes.

2.13 Starch in synthetic polymers

In the polymer sector, the following fields of application can be envisaged: the use of starch degradation products in the processing process (starch only acts as filler, there is no direct bond between the synthetic polymer and the starch) or, alternatively, the use of starch degradation products in the production of polymers (starch and polymer form a stable bond).

The use of starch as a pure filler is not competitive in comparison with other substances such as talc. However, this is different when the specific properties of starch make an impact and thus markedly alter the spectrum of characteristics of the end products. An example of this is the use of starch products in the processing of thermoplastics, such as polyethylene. Here, the starch and the synthetic polymer are combined by coexpression in a ratio of 1:1 to give a master batch, from which various products are produced with granulated polyethylene, using conventional process techniques. By using starch in polyethylene films, an increased substance permeability in the case of hollow bodies, an improved permeability for water vapor, an improved antistatic behavior, an improved antiblock behavior and an improved printability with aqueous inks can be achieved.

Another possibility is the use of starch in polyurethane foams. By adapting the starch derivatives and by process-engineering optimization, it is possible to control the reaction between synthetic polymers and the starches' hydroxyl groups in a directed manner. This results in polyurethane films which have the following spectrum of properties, owing to the use of starch: a reduced heat expansion coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens, or else reduced aging. Disadvantages which still exist are reduced printability and reduced impact strength.

Product development is currently no longer restricted to films. Solid polymer products such as pots, slabs and dishes which have a starch content of over 50% may also be produced. Moreover, starch/polymer mixtures are considered advantageous since their biodegradability is much higher.

Starch graft polymers have become exceedingly important owing to their extremely high water binding capacity. They are products with a starch backbone and a side lattice of a synthetic monomer, grafted on following the principle of the free-radical chain mechanism. The starch graft polymers which are currently available are distinguished by a better binding and retention capacity of up to 1000 g of water per g of starch combined with high viscosity. The fields of application of these superabsorbers have extended greatly in recent years and are, in the hygiene sector, products such as diapers and pads and, in the agricultural sector, for example seed coatings.

What is decisive for the application of novel, genetically modified starches are, on the one hand, structure, water content, protein content, lipid content, fiber content, ash/phosphate content, arnyose/amylopectin ratio, molecular mass distribution, degree of branching, granule size and granule shape and crystallinity, and, on the other hand, also the characteristics which effect the following features: flow and sorption behavior, gelatinization temperature, viscosity, viscosity stability in salt solutions, thickening power, solubility power, gel structure and gel transparency, thermal stability, shear stability, stability to acids, tendency to undergo retrogradation, gel formation, freeze-thaw stability, complex formation, iodine binding, film formation, adhesive power, enzyme stability, digestibility and reactivity.

The production of modified starches by recombinant methods can, on the one hand, alter the properties of the starch derived from the plant in such a way that other modifications by means of chemical or physical processes are no longer required. On the other hand, starches which have been altered by recombinant methods may be subjected to further chemical modification, which leads to further improvements in quality for some of the above-described fields of application. These chemical modifications are known in principle. They are, in particular, modifications by thermal treatment, treatment with organic or inorganic acids, oxidation and esterifications, which lead, for example, to the formation of phosphate starches, nitrate starches, sulfate starches, xanthate starches, acetate starches and citrate starches. Moreover, mono- or polyhydric alcohols in the presence of strong acids may be employed for producing starch ethers, resulting in starch alkyl ethers, O-allyl ethers, hydroxyalkyl ethers, O-carboxy methyl ethers, N-containing starch ethers, P-containing starch ethers), S-containing starch ethers, crosslinked starches or starch graft polymers.

A preferred use of the starches according to the invention is the production of packaging materials and disposable articles, on the one hand, and as foodstuff or foodstuff precursor on the other hand.

To express the nucleic acid molecules according to the invention in sense or antisense orientation in plant cells, they are linked to regulatory DNA elements which ensure transcription in plant cells. These include, in particular, promoters, enhancers and terminators. In general, any promoter which is active in plant cells is suitable for expression.

The promoter may be chosen in such a way that expression is constitutive or takes place only in a particular tissue, at a particular point in time of plant development or at a point in time determined by external factors. Relative to the plant, the promoter can be homologous or heterologous. Examples of suitable promoters are the cauliflower mosaic virus 35S RNA promoter and the maize ubiquitin promoter for constitutive expression, the patatin promoter B33 (Rocha-Sosa et al., EMBO J. 8 (1989), 23–29) for tuber-specific expression, or a promoter which ensures expression only in photosynthetically active tissue, for example the ST-LS1 promoter (Stockhaus et al., Proc. Natl. Acad. Sci. USA 84 (1987), 7943–7947; Stockhaus et al., EMBO J. 8 (1989), 2445–2451) or, for endosperm-specific expression, the wheat AMG promoter, the USP promoter, the phaseolin promoter or promoters from maize zein genes.

A termination sequence which serves to correctly terminate transcription and to add a poly-A tail to the transcript, which is considered to have a function in stabilizing the transcripts, may also be present. Such elements have been described in the literature (cf. Gielen et al., EMBO J. 8 (1989). 23–29) and are exchangeable as desired.

The present invention provides nucleic acid molecules which encode a protein with a wheat isoamylase function. The nucleic acid molecules according to the invention permit the production of this enzyme whose functional identification in starch biosynthesis, the generation of plants which have been altered by recombinant technology in which the activity of this enzyme is altered and thus allows a starch to be synthesized in plants modified thus whose structure is altered and whose physicochemical properties are altered.

In principle, the nucleic acid mnolecules according to the invention may also be used for generating plants in which the activity of the isoamylase according to the invention is increased or reduced while simultaneously the activities of other enzymes which participate in starch synthesis are altered. Altering the activities of an isoamylase in plants results in the synthesis of a starch with altered structure. Furthermore, nucleic acid molecules which encode an isoamylase or suitable antisense constructs can be introduced into plant cells in which the synthesis of endogenous starch synthases or branching enzymes is already inhibited (as, for example, in WO 92/14827 or Shannon and Garwood, 1984, in Whistler, BeMiller and Paschall, Starch: Chemistry and Technology, Academic Press, London, 2nd Edition: 25–86).

If it is intended to achieve the inhibition of the synthesis of several enzymes involved in starch biosynthesis in transformed plants, the transformation may involve DNA molecules which simultaneously comprise several regions encoding the enzymes in question in antisense orientation under the control of a suitable promoter. Here, it is possible for each sequence to be under the control of its own promoter, or for the sequences to be transcribed by a joint promoter as a fusion or to be under the control of a joint promoter. The last-mentioned alternative will generally be preferred, since in this case the synthesis of the proteins in question should be inhibited roughly to the same extent. As regards the length of the individual coding regions used in such a construct, what has been mentioned above for the generation of antisense constructs also applies here. In principle, there is no upper limit for the number of antisense fragments to transcribed in such a DNA molecule starting from one promoter. However, the transcript formed should preferably not exceed a length of 10 kb, in particular a length of 5 kb.

Coding regions localized in such DNA molecules in combination with other coding regions in antisense orientation behind a suitable promoter may be derived from DNA sequences which encode the following proteins: starch-granule-bound starch synthases (GBSS I and II) and soluble starch synthases (SSS I and II), branching enzymes (isoamylases, pullulanases, R enzymes, branching enzyrnes, debranching enzymes), starch phosphorylases and disproportioning enzymes. This enumeration is only by way of example. The use of other DNA sequences for the purposes of such a combination is also feasible.

Such constructs allow the synthesis of a plurality of enzymes to be inhibited simultaneously in plant cells transformed with them.

Furthermore, the constructs can be introduced into plant mutants which are deficient for one or more starch biosynthesis genes (Shannon and Garwood, 1984, in Whistler, BeMiller and Paschall, Starch: Chemistry and Technology, Academic Press, London, 2nd Edition: 25–86). These defects may relate to the following proteins: starch-granule-bound starch synthases (GBSS I and II) and soluble starch synthases (SSS I and II), branching enzymes (BE I and II), debranching enzymes (R enzymes), disproportioning enzymes and starch phosphorylases. This enumeration is only by way of example.

Such a procedure furthermore allows the synthesis of a plurality of enzymes to be inhibited simultaneously in plant cells transformed with them.

To prepare the introduction of foreign genes into higher plants, a large number of cloning vectors containing a replication signal for *E.coli* and a marker gene for selecting transformed bacterial cells is available. Examples of such vectors are pBR322, pUC series, M13mp series, pACYC184 and the like. The desired sequence may be introduced into the vector at a suitable restriction cleavage site. The plasmid obtained is used to transform *E.coli* cells. Transformed *E.coli* cells are grown in a suitable medium and subsequently harvested and lyzed. The plasmid is recovered. Analytical methods for characterizing the plasmid DNA obtained which are generally used are restriction analyses, gel electrophoresls and further methods of biochemistry and molecular biology. After each manipulation, the plasmid DNA can be cleaved and resulting DNA fragments linked to other DNA sequences. Each plasmid DNA sequence can be cloned in identical or different plasmids.

A large number of techniques is available for introducing DNA into a plant host cell. These techniques encompass transformation of plant cells with t-DNA using Agrobacterium tumefaciens or Agrobacterium rhizogenes as transformation agents, protoplast fusion, injection, the electroporation of DNA, the introduction of DNA by means of the biolistic method, and other possibilities.

The injection and electroporation of DNA into plant cells per se require no particular aspect of the plasmids used. Simple plasmids such as, for example, pUC derivatives may be used. However, if intact plants are to be regenerated from such transformed cells, the presence of a selectable marker gene is generally required.

Depending on the method of introducing desired genes into the plant cell, further DNA sequences may be required. If, for example, the Ti or Ri plasmid is used for transforming the plant cell, at least the right border, but frequently the right and left borders, of the Ti and Ri plasmid T-DNA must be linked to the genes to be introduced as flanking region.

If agrobacteria are used for the transformation, the DNA to be introduced must be cloned into specific plasmids, either into an intermediate vector or into a binary vector. The intermediate vectors can be integrated into the agrobacterial Ti or Ri plasmid by homologous recombination owing to sequences which are homologous to sequences in the T-DNA. The former also contains the vir region, which is required for the T-DNA transfer. Intermediate vectors cannot replicate in agrobacteria. The intermediate vector can be transferred to Agrobacterium turnefaciens (conjugation) by means of a helper plasmid. Binary vectors are capable of replication in *E.coli* and in agrobacteria. They contain a selection marker gene and a linker or polylinker, which are framed by the left and right T-DNA border regions. They can be transformed directly into the agrobacteria (Holsters et al. Mol. Gen. Genet. 163 (1978), 181–187). The agrobacterium which acts as the host cell should contain a plasmid carrying a vir region. The vir region is required for transferring the T-DNA into the plant cell. Additional T-DNA may be present. The agrobacterium thus transformed can be used for transforming plant cells.

The use of T-DNA for transforming plant cells has been researched intensively and been described in EP 120 516; Hoekema, in: The Binary Plant Vector System Offsetdrukkerij Kanters B. V., Alblasserdam (1985), Chapter V; Fraley et al., Crit. Rev. Plant Sci., 4, 1–46 and An et al. EMBO J. 4 (1985). 277–287.

To transfer the DNA into the plant cell, plant explants can expediently be cocultured with Agrobacterium tumefaciens or Agrobacterium rhizogenes. Intact plants can then be regenerated again from the infected plant material (for example leaf sections, stalk sections, roots, but also protoplasts, or plant cells grown in suspension culture) in a suitable medium which can contain, inter alia, certain sugars, amino acids, antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L, 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basel-Cambridge).

While the transformation of the dicotyledonous plants via Ti-plasmid vector systems with the aid of Agrobacterium tumefaciens is well established, more recent work suggests that even monocotyledonous plants are indeed accessible to transformation by means of agrobacterium-based vectors (Chan et al., Plant Mol. Biol. 22 (1993), 491–506; Hiei et al., Plant J. 6 (1994), 271–282).

Alternative methods for the transformation of monocotyledonous plants are the transformation by means of the biolistic approach, protoplast transformation, or the physically- or chemically-induced DNA uptake into protoplasts, for example by electroporation of partially permeabilized cells, transfer of DNA by means of glass fibers, macroinjection of DNA into inflorescences, the microinjection of DNA into microspores or proembryos, DNA uptake by germinating pollen and DNA uptake in embryos by swelling (review: Potrykus, Physiol. Plant (1990), 269–273).

Three of the abovementioned transformation systems have been established in the past for various cereals: the electroporation of tissue, the transformation of protoplasts and the DNA transfer by particle bombardment into regenerable tissue and cells (review: Jahne et al., Euphytica 85 (1995). 35–44).

Different methods of transforming wheat have been described in the literature (review: Maheshwari et al., Critical Reviews in Plant Science 14 (2) (1995), 149 to 178): Hess et al. (Plant Sci. 72 (1990), 233) employ the macroinjection method to bring pollen and agrobacteria into the immediate vicinity. The mobilization of the plasmid which contained the nptll gene as selectable marker was detected by Southern blot analysis and NPTll test. The transformants showed a normal phenotype and were fertile. Kanamycin resistance was detected in two consecutive generations.

The first transgenic fertile wheat plant which was regenerated after bombardment with DNA bound to microprojecliles was described by Vasil et al. (Bio/Technology 10 (1992), 667–674). The target tissue for the bombardment was an embryogenic callus culture (type C callus). The selection marker employed was the bar gene which encodes a phosphinothricin acetyl transferase and thus mediates resistance to the herbicide phosphinothricin. A further system was described by Weeks et al. (Plant Physiol. 102 (1993), 1077–1084), and Becker et al. (Plant J. 5(2) (1994), 299–307). Here, the target tissue for the DNA transformation is the scutellum of immature embryos which was stimulated in a preliminary in-vitro phase to induce somatic embryos. The transformation efficacy in the system developed by Becker et al. (loc cit.) is 1 transgenic plant per 83 embryos of the variety "Florida" and thus markedly higher than the system established by Weeks et al., which yields 1 to 2 transgenic plants per 1000 embryos of the variety "Bohwhite".

The system developed by Becker et al. (loc Cit) forms the basis for the transformation experiments described in the examples.

Once the DNA introduced is integrated into the genome of the plant cell, it a is, as a rule, stable and is also retained in the progeny of the originally transformed cell. It normally contains one of the above-mentioned selection markers which mediates, for example, resistance to a biocide such as phosphinothricin or an antibiotic such as kanamycin, G 418, bleomycin or hygromycin, to the transformed plant cells or which permits selection via the presence or absence of certain sugars or amino acids. The marker chosen individually should therefore allow the selection of transformed cells over cells which lack the DNA introduced.

Within the plant, the transformed cells grow in the customary manner (see also McCormick et al., Plant Cell Reports 5 (1986), 81–84). The resulting plants can be grown normally and hybridized with plants which have the same transformed germ plasm or other germ plasm. The resulting hybrid individuals have the corresponding phenotype properties. Seeds may be obtained from the plant cells. Two or more generations should be grown in order to ensure that the phenotype characteristic is stably retained and inherited. Also, seeds should be harvested in order to ensure that the phenotype in question or other characteristics have been retained.

The examples which follow are intended to illustrate the invention and do not constitute any restriction whatsoever.

1. Cloning methods
   The vector pBluescript II SK (Stratagene) was used for cloning in E.coli.
2. Bacterial strains
   The E. coli strain DH5α (Bethesda Research Laboratories, Gaithersburg, USA) was used for the Bluescript vector and for the anfisense constructs. The E. coli strain XL1-Blue was used for the in vivo excision.
3. Transformation of immature wheat embryos

| Media | | |
|---|---|---|
| MS: | 100 ml/l macrosalt<br>1 ml/l microsalt<br>2 ml/l Fe/NaEDTA<br>30 g/l sucrose | (D. Becker and H. Lörz, Plant Tissue Culture Manual (1996), B 12:1–20) |
| #30: | MS + 2,4-D (2 mg/l) | |
| #31: | MS + 2,4-D (2 mg/l) + phosphinothricin (PPT, active component of herbicide BASTA (2 mg/l)) | |
| #32: | MS + 2,4-D (0.1 mg/l) + PPT (2 mg/l) | |
| #39: | MS + 2,4-D (2 mg/ml) + of each 0.5 N mannitol/sorbitol | |

The media stated were brought to pH 5.6 using KOH and solidified using 0.3% Galrita.

The method for transforming immature wheat embryos was developed and optimized by Becker and Lörz (D. Becker and H. Lörz, Plant Tissue Culture Manual (1996). B12: 1 to 20).

In the experiments described hereinbelow, the procedure developed by Becker and Lörz (loc. Cit) was adhered to.

For the transformation, ears with caryopses of developmental stage 12 to 14 days after anthesis were harvested and surface-sterilized. The isolated scutella were plated onto induction medium #30 with the embryo axis orientated toward the medium.

After preculture for 2 to 4 days (26° C., in the dark), the explants are transferred to medium #39 for the osmotic preculture (2 to 4 h, 26° C., in the dark).

For the biolistic transformation, approx. 29 μg of gold particles on which a few μg of the target DNA had previously been precipitated were employed per shot. Since the experiments carried out are cotransformants, the target DNA composed of the target gene and a resistance marker gene (bar gene) in the ratio 1:1 is added to the precipitation batch.

4. DIG labeling of DNA fragments

DNA fragments employed as screening probes were labeled via a specific PCR with the incorporation of DIG-labeled dUTP (Boehringer Mannheim, Germany).

Media and solutions used in the examples:
20×SSC 3175.3 g NaCl
  88.2 g sodium citrate
  twice-distilled $H_2O$ to 1000 ml
  10 N NaOH to pH 7.0

Plasmid pTaSU 8A was deposited at the DSMZ in Braunschweig, Federal Republic of Germany, as specified in the Budapest Treaty under the No. DSM 12795, and plasmid pTaSU 19 under the No. DSM 12796.

EXAMPLE 1

Identification, Isolation and Characterization of a cDNA Encoding an Isoamylase ("Sugary" Homolog) from Wheat (*Trifcum aestivum L.*, cv Florida)

To identify a cDNA which encodes a wheat isoamylase isoform (sugary), a heterologous screening strategy was followed. To this end, a wheat cDNA library was screened with a maize sugary probe.

The probe (sugary probe) was isolated from a maize cDNA library by means of specific primers using PCR amplification. The maize cDNA library was cloned from poly(A)+RNA from a mixture of equal amounts of 13-, 17-, 9-, 20-, 22-, 25- and 28-day (DAP) old caryopses in a Lambda Zap II vector following the manufacturer's instructions (Lambda ZAP II-cDNA Synthesis Kit Stratagene GmbH, Heidelberg, Germany). In all the caryopses used, with the exception of the 13-day-old kemels, the embryo had been removed prior to isolating the RNA.

The DNA fragment employed as a probe for screening the wheat cDNA library was amplified with the following primers:
sulp-1:5'-AAAGGCCCAATATTATCCTTTAGG-3' (SEQ ID NO:4) sulp-2:5'-GCCATTTCAACCGTTCTGAAG-TCGGGAAGTC-3' (SEQ ID NO:5)

The template employed for the PCR reaction was 2 µl of the amplified maize cDNA library. Furthermore, the PCR reaction contained 1.5–3 mM $MgCl_2$, 20 mM Tris-HCl (pH 8.4), 50 mM KCl, 0.8 mM dNTP mix, 1 µM primer sulp-1a, 1 µM primer sulp-2 and 2.5 units Taq polymerase (recombinant, Life Technologies).

The amplification was carried out using a Trioblock from Biometra following the scheme: 4 min/95° C.; 1 min/95° C., 45 sec/58° C.; 1 min 15 sec/72° C.;30 cycles 5 min/72° C. The amplified DNA band of approx. 990 bp was separated in an agarose gel and excised. A second amplification was [lacuna] from this fragment following the scheme as described above. The 990 bp fragment obtained from this second amplificaton was cleaved with the restriction enzyme BAM HI into a 220 bp and a 770 bp fragment After the sugary fragment had again been separated in an agarose gel, the band excised and the fragment isolated, the probe was DIG-labeled. 500 ng of sugary fragment were employed for the random-prime labeling with digoxygenin. 10 µl of random primer were added to the fragment to be labeled and the reaction was heated for 5 min at 95–100° C. After heating, 0.1 mM dATP, 0.1 mM dGTP, 0.1 mM dCTP and 0.065 mM dTTP and 0.035 mM digoxygenin-11-dUTP (Boehringer Mannheim) and Klenow buffer (standard) and 1 unit of Klenow polymerase were added. The reaction was allowed to proceed at RT (room temperature) overnight. To check the labeling, a dot test was carried out following the manufacturer's instructions ("The DIG System User's Guide for Filter Hybridization" by Boehringer, Mannheim, Germany).

The wheat cDNA library was synthesized from poly(A)+ RNA of approx. 21day ("starchy" endosperm) old caryopses in a Lamda Zap II vector following the manufacturer's instructions (Lambda ZAP II-cDNA Synthesis Kit, Stratagene GmbH, Heidelberg). After determination of the titer of the cDNA library, a primary titer of $1.26 \times 10^6$ pfu/ml was determined.

To screen the wheat cDNA library, approx. 350,000 phages were plated out. The phages were plated out and the plates blotted by standard protocols. The filters were prehybridized and hybridized in 5×SSC, 3% blocking (Boehringer, Mannheim), 0.2% SDS, 0.1% sodium laurylsarcosin and 50 µl/ml herring sperm DNA at 55° C. 1 ng/ml of the labeled sugary probe was added to the hybridization solution and the hybridizabon was incubated overnight. The filters were washed 2×5 mins in 2×SSC, 1% SDS at RT; 2×10 min in 1×SSC, 0.5% SDS at 55° C.; 2×10 min in 0.5×SSC, 0.2% SDS at 55° C. Positive clones were singled out by further screening cycles. Single clones were obtained via in vivo excision as pBluescript SK phagerids (prowedure analogous to the manufacturer's instructions; Stratagene, Heidelberg, Genmany).

After the clones had been analyzed via minipreps and restriction of the plasmid DNA, clone pTaSU-19 was deposited at the DSMZ Deutsche Sammlung für Mikroorganismen und Zellkulturen GmbH under the number DSM 12796 and analyzed in greater detail.

EXAMPLE 2

Sequence Analysis of cDNA Insertions of Plasmids pTaSU19

The plasmid DNA was isolated from done pTaSU19 and the sequence of the cDNA insertions determined by means of the dideoxynucleotide method (Sanger et al., Proc. Natl. Acad. Sci. USA 74 (1977), 5463–5467).

The insertion of clone TaSU-19 is 2997 bp in length and constitutes a partial cDNA. The nucleotide sequence is shown under SEQ ID NO:2. A comparison with already published sequences revealed that the sequence shown under SEQ ID NO:2 encompasses a coding region which has homologies to isoamylases from other organisms.

Sequence analysis also reveals that two introns are located in the cDNA sequence in position 297–396 (intron 1) and 1618–2144 (intron 2). If these introns are removed, a protein sequence may be derived which exhibits homologies to the protein sequences of isoamylases of other organisms. The amino acid sequence which corresponds to the coding regions of SEQ ID NO:2 is shown under SEQ ID NO:3.

EXAMPLE 3

Generation of the Plant Transformation Vector pTa-alpha-SU19

To express an antisense RNA corresponding to the TaSU19-cDNA, the plant transformation vectors pTa-alpha-SU19 were constructed on the basis of the basic plasmid pUC19 by linking the cDNA insertion of plasmid pTa-alpha-SU19 in antisense orientation to the 3' end of the ubiquitin promoter. This promoter is composed of the first untranslated exon and the first intron of the maize ubiquitin 7 gene (Christensen A. H. et al., Plant Molecular Biology 19 (1992), 675–689). Parts of the polylinker and the NOS terminator are derived from plasmid pAct1.cas (CAMBIA, TG 0063; Cambia, GPO Box 3200, Canberra ACT 2601, Australia). Vector constructs with this terminator and constructs based on pAct1.cas are described by MCElroy et al. (Molecular Breeding 1 (1995), 27–37). The vector thus formed was termed pUbi.cas.

The vector was cloned by restricting a 2kb fragment from clone Ta-SU19 with the restriction enzyme Xba I. The fragment was filled up at the ends by means of Klenow reaction and subsequently ligated into the Sma I cloning site of the expression vector pUbi.cas.

The resulting expression vector is termed Ta-alpha-SU 19 and is used as described above for transforming wheat.

EXAMPLE 4

Isolation and Characterization of a Further cDNA Encoding an isoamylase (Sugary 1 Homolog) from Wheat (*Tritilcum aestivum* L., cv Florida)

A wheat cDNA library was screened with a sugary probe which represents a part of clone pTaSU19, viz. positions 489–1041 of SEQ ID NO: 1

The wheat-specific digoxygemin-labeled sugary probe employed for screening the cDNA library was prepared by means of PCR amplification. The primers employed in this reaction were:

SUSO1:5'-GCT TTA CGG GTA CAG GTT CG-3' (SEQ ID NO:8), and

SUS2:5'-AAT TCC CCG TTT GTG AGC-3' (SEQ ID NO:9)

1 ng of plasmid pTaSU19 was employed in the reaction as tempiate. In addition, the PCR reaction contained in each case 300 nM of the primers SUS01 and SUS02, in each case 100 $\mu$M of the nucleotides DATP, dGTP, dCTP, 65 $\mu$M DTTP, 35 $\mu$M digoxygeninri 1-dUTP (Boehringer Mannheim), 1.5 mM MgCl$_2$, and 2.5 U (units) Taq polymerase and 10 $\mu$l of 10-fold concentrated Taq polymerase reaction buffer (both Life Technologies). The final volume of the reaction was 100 $\mu$l. The amplification was performed in a PCR apparatus (TRIO® Thermoblock, Biometra) with the following temperature regime: 3 min at 95° C. (once); 45 sec at 95° C.—45 sec at 55° C.—2 min at 72° C. (30 cycles); 5 min at 72° C. (once). A 553 bp DNA fragment resulted. The incorporation of dogoxygenin-11-dUTP into the PCR product was revealed owing to the reduced mobility in the agarose gel in comparison with the product of a controlled reaction without digoxygenin-11-dutp.

The caryopses-specific wheat cDNA library of Example 1 was screened with the resulting digoxygenin-labeled probe.

The hybridization step was performed overnight in 5×SSC, 0.2% SDS. 0.1% sodium laurylsarcosin and 50 $\mu$g/ml herring sperm DNA at 68° C. in the presence of 1 ng/ml of the digoxygenin-labeled probe. After the hybridization, the filters were washed as follows: 2×5 min in 2×SSC, 1% SDS at RT; 2×10 min in 1×SSC, 0.5% SDS at 68° C.; 2×10 min in 0.5×SSC, 0.2% SDS at 68° C. Positive clones were singled out by at least two further screening cycles. Plasmids were obtained from the phage clones pBluescript SK via in vivo excision (protocols in accordance with the manufacturer's instructions; Stratagene, Heidelberg, Germany). After restriction analysis it clones obtained, clone pTaSU8A was deposited at the Deutsche Sammlung für Mikroorganismen und Zellkulturen under the number DSM 12795 and studied in greater detail.

EXAMPLE 5

Sequence Analysis of the cDNA Inset in Plasmid pTaSU8A

The nucleotide sequence of the cDNA insert in plasmid pTaSU8A was determined by means of the dideoxynucleotide method (SEQ ID NO:6).

The insertion of clone pTaSU8A is 2437 bp in length and constitutes a partial cDNA. A comparison with already published sequences reveals that the sequence shown under SEQ ID NO:6 comprises a coding region which has homologies to isoamylases from other organisms. Equally, the protein sequence derived from the coding region of clone pTaSU8A and shown in SEQ ID NO:7 exhibits homologies to the protein sequences of isoamylases of other organisms. Upon comparison of the sequences of clones pTaSU19 (SEQ ID NO:1) and pTaSU8A (SEQ ID NO:6), a similarity of 96.8% results. Most of the differences regarding the sequences are in the 3'-untranslated region of the cDNAs. The remaining differences regarding the sequences in the coding region lead to different amine acids at a total of 12 positions of the derived protein sequences SEQ ID NOs:3 and 7. The cDNAs contained in pTaSU19 and pTaSU8A are not identical and encode isoforms of the wheat isoamylase.

EXAMPLE 6

Generation of the Plant Transformation Vector pTa-alpha-SU8A

To express an antisense RNA corresponding to the TaSU8A cDNA, the plant transformation vector pTa-alpha-SU8A was constructed on the basis of the basic plasmid pUC19 by linking a part of the TaSU8A cDNA generated by PCR amplification in antisense orientation to the 3' end of the ubiquitin promoter. This promoter is composed of the first untranslated exon and the first intron of the maize ubiquitin I gene (Christensen A. H. et al., Plant Mol. Biol 1 (1992), 675–689). Parts of the polylinker and the NOS terminator are derived from plasmid pAct1.cas (CAMBIA, TG 0063; Cambia, GPO Box 3200, Canberra ACT 2601, Australia). Vector constructs with this terminator and constructs based on pAct1.cas are described by McElroy et al. (Molecular Breeding 1 (1995), 27–37). The vector containing ubiquitin promoter, polylinker and NOS terminator and based on pUC19 was termed pUbi.cas.

To clone pTa-alpha-SU8A, an approx. 2.2 kb portion of the TaSU8A cDNA, viz. positions 140–2304 of SEQ ID NO:6 was amplified by means of PCR.

The primers employed in this reaction were:

SUEX3:5'-GCG GTA CCT CTA GAA GGA GAT ATA CAT ATG GCG GAG GAC AGG TAC GCG CTC-3' SEQ ID NO:10, and

SUEX4:5'-GCT CGA GTC GAC TCA AAC ATC AGG GCG CAA TAC-3' SEQ ID NO:11.

1 ng of plasmid pTaSU8A was employed in the reaction as template. In addition, the PCR reaction contained: in each case 300 nM of the primers SUEX3 and SUEX4, in each case 200 $\mu$M of the nucleotides dATP, dGTP, dCTP and dTTP, 1.6 mM MgCl$_2$, 60 mM Tris-SO$_4$ (pH 9.1), 18 mM (NH$_4$)$_2$SP$_4$ and 1 $\mu$l of Elongase® enzyme mix (mixture of Taq polymerase and DNA polymerase, Life Technologies). The final volume of the reaction was 50 $\mu$l. Amplification was performed in a PCR apparatus (TRIO® Thermoblock, Biometra) with the following temperature regime: 1 min at 94° C. (once); 30 sec at 95° C.—30 sec at 55° C.—2 min 30 sec at 68° C. (30 cycles); 10 min at 68° C. (once). The reaction gave rise to a DNA fragment 2205 bp in length.

The 22 kb product was restricted with Kpnl and Sall and ligated into the expression vector pUbi.cas which had previously been cleaved with Kpnl and Sall. The resulting plant transformation vector was termed pTa-alpha-SU8A and used as described above for transforming wheat.

We claim:

1. An isolated nucleic acid molecule encoding a protein with the function of a wheat isoamylase, selected from the group consisting of
   (a) a nucleic acid molecule encoding a protein comprising the amino acid sequence of SEQ ID NO:3,
   (b) a nucleic acid molecule comprising the nucleotide sequence of SEQ ID NO:2 or a ribonucleotide sequence corresponding thereto; and
   (c) a nucleic acid molecule whose nucleotide sequence deviates from the sequence of a nucleic acid molecule mentioned under (a) or (b) owing to the degeneracy of the genetic code,
   wherein the isolated nucleic acid molecule is isolated from wheat.

2. An isolated nucleic acid molecule which hybridizes with the complement of the nucleic acid molecule of claim 1, wherein the hybridization conditions comprise a hybridization temperature of 68° C., a hybridization buffer salt concentration of 5×SSC, a wash temperature of 68° C., and a wash buffer salt concentration of 0.5×SSC, wherein the isolated nucleic acid molecule encodes a wheat isoamylase.

3. The nucleic acid molecule as claimed in claim 1 which is a DNA molecule.

4. The nucleic acid molecule as claimed in claim 3 which is a cDNA molecule.

5. The nucleic acid molecule as claimed in claim 1 comprising regulatory elements.

6. The nucleic acid molecule as claimed in claim 1 which is an RNA molecule.

7. A vector containing the DNA molecule as claimed in claim 1.

8. The vector as claimed in claim 7, wherein said nucleic acid molecule is operably linked in sense orientation to regulatory elements which ensure transcription and synthesis of a translatable RNA in prokaryotic or eukaryotic cells.

9. A host cell which is transformed with the nucleic acid molecule as claimed in claim 1, or transformed with a vector comprising the nucleic acid molecule of claim 1, or a cell which is derived from the host cell, which derived cell comprises said nucleic acid molecule.

10. A process for the preparation of a protein encoded by the nucleic acid molecule as claimed in claim 1, wherein a host cell transformed with the nucleic acid molecule of claim 1 or transformed with a vector comprising said nucleic acid molecule is cultured under conditions which permit said protein to be synthesized and said protein is isolated from the cultured cells and/or the culture medium.

11. A process for generating a transgenic plant cell, wherein
   a) the nucleic acid molecule as claimed in claim 1 or
   b) a vector comprising said nucleic acid molecule is integrated into the genome of a plant cell.

12. A transgenic plant cell which has been transformed with the nucleic acid molecule as claimed in claim 1 or transformed with a vector comprising the nucleic acid molecule of claim 1, or a cell which is derived from the transgenic plant cell, which derived cell comprises said nucleic acid molecule.

13. A process for generating a transgenic plant cell, wherein
   a1) the nucleic acid molecule as claimed in claim 1 or
   a2) a vector comprising the nucleic acid molecule of claim 1 is integrated into the genome of a plant cell and
   b) an intact plant is regenerated from said plant cell.

14. A plant containing the plant cell as claimed in claim 12.

15. The plant as claimed in claim 14 which is a crop plant.

16. The plant as claimed in claim 15 which is a starch-storing plant.

17. The plant as claimed in claim 16 which is a monocotyledonous plant or maize.

18. The plant as claimed in claim 17 which is a barley, rye or wheat plant.

19. Propagation material of the plant as claimed in claim 14, wherein said propagation material comprises said nucleic acid molecule.

20. A process for the production of strch comprising isolating starch frrom the cell as claimed in claim 12, the plant as claimed in claim 14 or the propagation material as claimed in claim 19.

* * * * *